(12) United States Patent
McMinn

(10) Patent No.: US 11,612,487 B2
(45) Date of Patent: Mar. 28, 2023

(54) KNEE PROSTHESIS

(71) Applicant: Derek James Wallace McMinn, West Midlands (GB)

(72) Inventor: Derek James Wallace McMinn, West Midlands (GB)

( * ) Notice: Subject to any disclaimer, the term of this patent is extended or adjusted under 35 U.S.C. 154(b) by 350 days.

(21) Appl. No.: 16/675,639

(22) Filed: Nov. 6, 2019

(65) Prior Publication Data

US 2020/0069432 A1 Mar. 5, 2020

Related U.S. Application Data

(63) Continuation-in-part of application No. 14/590,426, filed on Jan. 6, 2015, now abandoned.

(30) Foreign Application Priority Data

Jan. 7, 2014 (GB) ...................................... 1400224
May 28, 2014 (GB) ...................................... 1409404

(51) Int. Cl.
*A61F 2/38* (2006.01)

(52) U.S. Cl.
CPC .......... *A61F 2/3854* (2013.01); *A61F 2/3859* (2013.01); *A61F 2/3868* (2013.01); *A61F 2002/3863* (2013.01); *A61F 2230/0041* (2013.01)

(58) Field of Classification Search
CPC .............................. A61F 2/3886; A61F 2/3854
See application file for complete search history.

(56) References Cited

U.S. PATENT DOCUMENTS

| | | | |
|---|---|---|---|
| 3,748,662 | A | 7/1973 | Helfet |
| 4,057,858 | A | 11/1977 | Helfet |
| 5,219,362 | A | 6/1993 | Tuke et al. |
| 5,964,808 | A | 10/1999 | Blaha et al. |
| 6,152,960 | A | 11/2000 | Pappas |
| 6,846,329 | B2 | 1/2005 | McMinn |
| 2005/0209701 | A1 | 9/2005 | Suguro et al. |
| 2008/0243258 | A1 | 10/2008 | Sancheti |
| 2009/0326663 | A1 | 12/2009 | Dun |

(Continued)

FOREIGN PATENT DOCUMENTS

| | | |
|---|---|---|
| DE | 3314038 A1 | 10/1983 |
| EP | 2165681 A1 | 3/2010 |

(Continued)

OTHER PUBLICATIONS

GB1409404.9, Examination Report under Section 18(3), dated Jan. 31, 2020.

(Continued)

*Primary Examiner* — Megan Y Wolf
(74) *Attorney, Agent, or Firm* — Morgan, Lewis & Bockius, LLP

(57) ABSTRACT

A knee prosthesis comprises a femoral component for securement to a femur, the femoral component defining medial and lateral J-shaped condyles and an intercondylar groove; and a fixed bearing tibial component for securement to a tibia, the tibial component having respective bearing surfaces which are fixed with respect to both a tibial engaging component and a stabilising peg for securing the tibial component to a tibia, the respective bearing surfaces being shaped to engage with said condyles both when the knee, in use, is extended and also over a range of flexion.

20 Claims, 29 Drawing Sheets

(56) References Cited

U.S. PATENT DOCUMENTS

2010/0191341 A1    7/2010   Byrd
2013/0197653 A1    8/2013   Hawkins et al.
2015/0190236 A1    7/2015   McMinn

FOREIGN PATENT DOCUMENTS

GB        2223950 A     4/1990
GB        2387546 A    10/2003
GB        2426201 A    11/2006
WO   2013007747 A1    1/2013

OTHER PUBLICATIONS

Nakamura et al., "Are the long term results of a high-flex total knee replacement affected by the range of flexion?" International Orthopaedics (SICOT), 38:761-766 (2014).
GB1409404.9, Search Report under Section 17, dated Dec. 16, 2014.

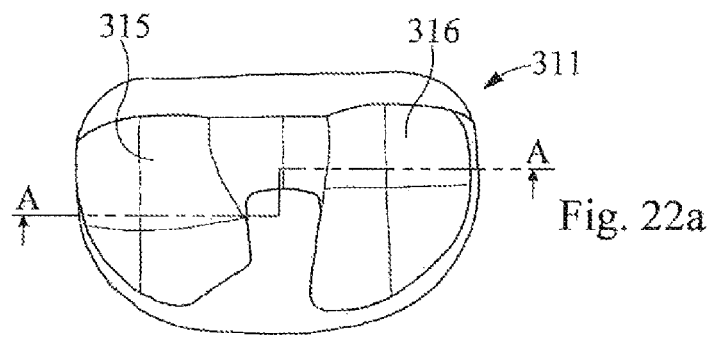
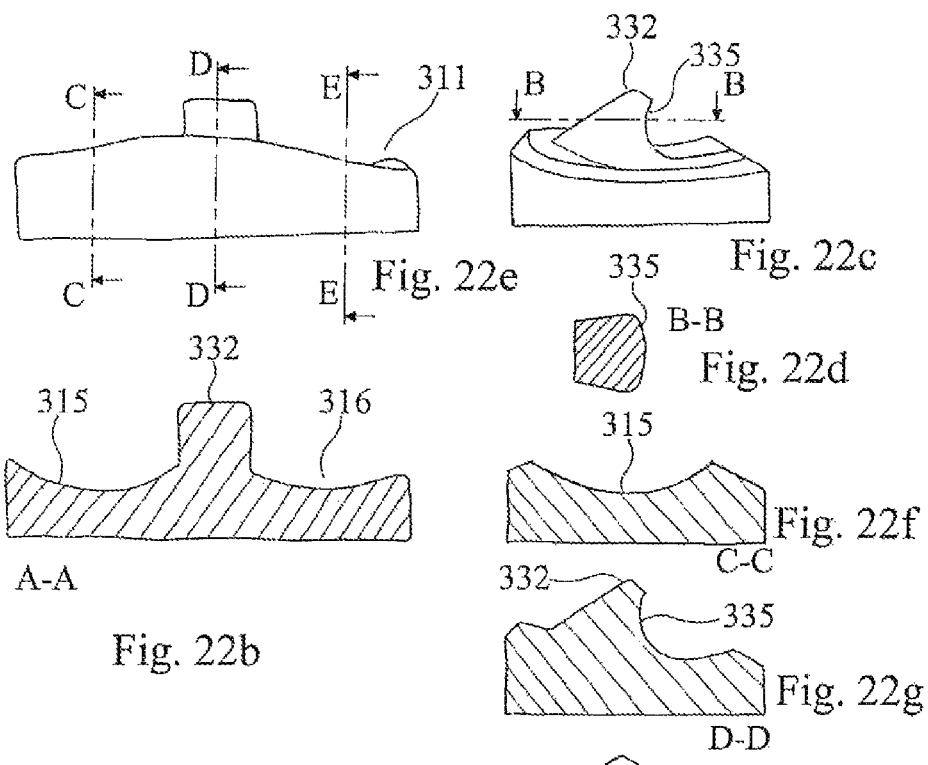
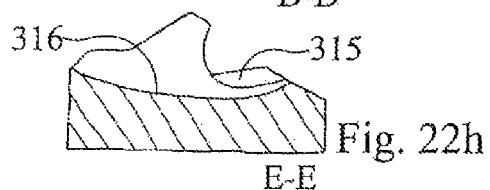

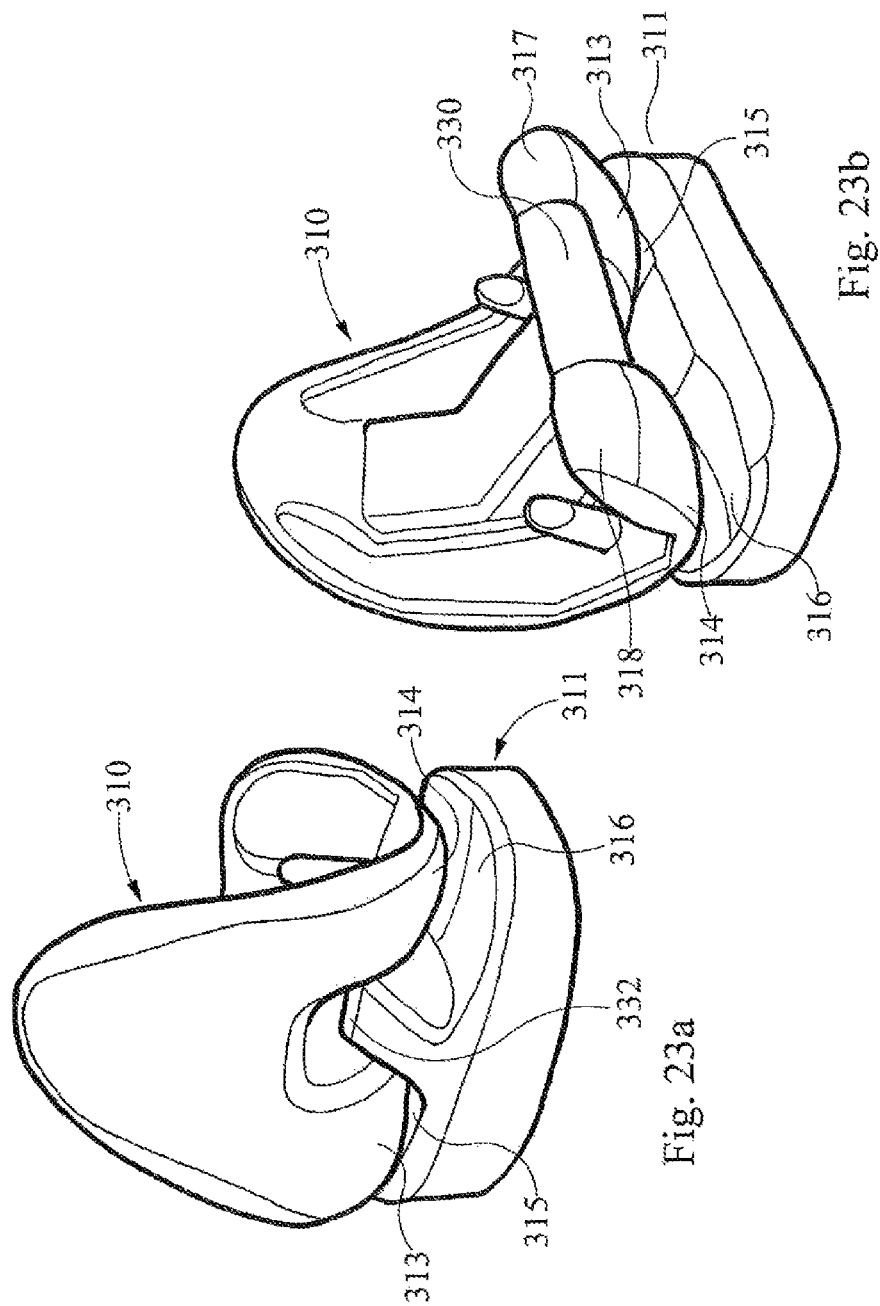

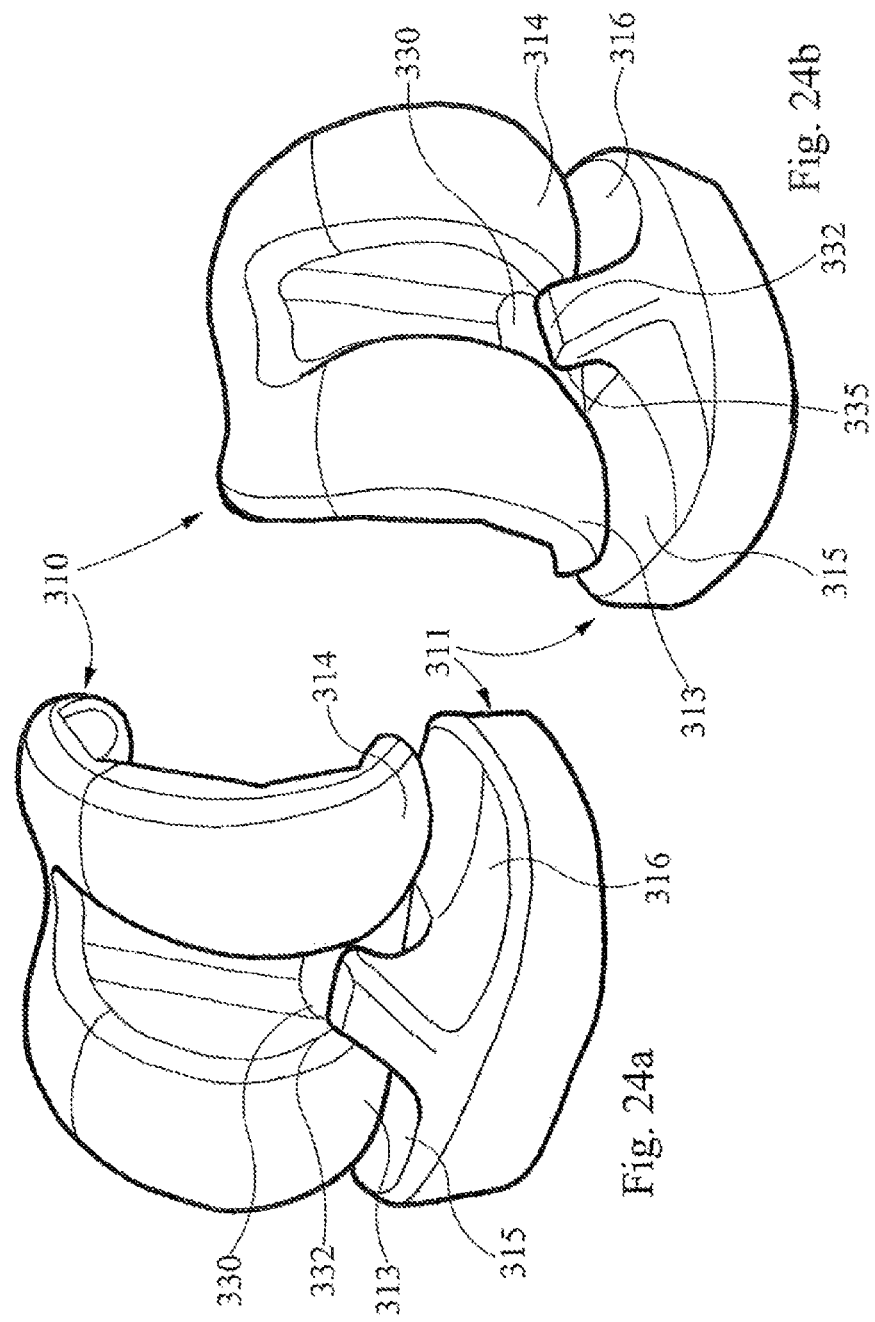

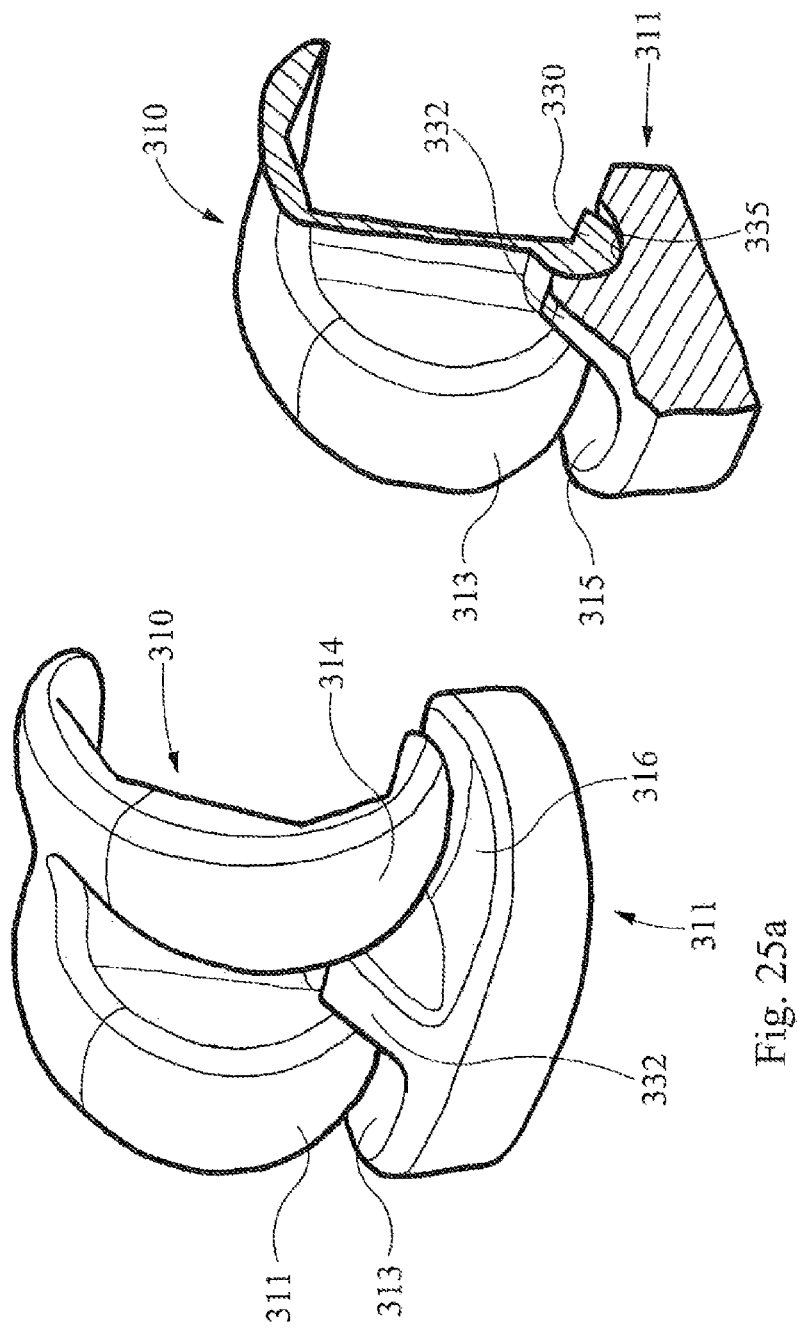

Side View 75 degrees of flexion

Side View
85 degrees of
flexion

Medial    Lateral

Side View
140 degrees of flexion

Medial  Lateral

KNEE PROSTHESIS

RELATED APPLICATIONS

This application is a continuation-in-part of U.S. patent application Ser. No. 14/590,426, filed Jan. 6, 2015, which claims the benefit of and priority to United Kingdom Patent Application No. 1400224.0, filed Jan. 7, 2014, and United Kingdom Patent Application No. 1409404.9, filed May 28, 2014. The entire disclosure of each of these applications is hereby incorporated by reference.

FIELD OF THE INVENTION

This invention relates to a knee prosthesis for fitting to a patient as a replacement knee joint.

BACKGROUND TO THE INVENTION

In a normal knee, the groove on the femur for the patella is laterally displaced with respect to the mid-point of the femur, this lateral displacement being of the order of 5 mm. In addition to being laterally displaced, the patella groove on the femur is laterally angulated by 7° with respect to the distal femur and knee joint.

In the normal knee therefore as it flexes, the patella articulates in the patella groove on the femur. Clearly it is thus important in knee replacement design to reproduce the natural position of the patella groove on the prosthetic femoral component. This is not presently reliably reproduced in many knee replacement designs, and lateral patella maltracking is a common cause of pain and morbidity. In one known design, part of the lateral femoral condyle prosthesis is removed to accommodate such lateral displacement of the groove. This is undesirable in producing a reduced area of contact between the lateral femoral condyle and the polyethylene articulating surface, with the potential for increased plastics wear.

In another known design the long axis of the femoral condyles is at right angles to the transverse axis of the knee joint. When the knee is extended, the patella articulates at the front of the femoral component. Since this area is not required for the tibia-femoral articulation, then metal can be removed to provide a lateral angulation to the patella groove. However, when the knee is flexed, the patella groove is the general area between the medial and lateral femoral condyles, and these condyles are involved in the tibia-femoral articulation in extension. Any attempt by a designer to angulate the patella groove will have serious detrimental effects. The more the patella groove is angulated and displaced, the more the area of articulation for the lateral femoral condyle is reduced.

In GB2387546B the Applicant proposed a new design of knee prosthesis to address the problems with the above. This design includes a mobile bearing component between the femoral and tibial components, the bearing component having respective surfaces shaped to match the femoral condyles and engage therewith both when the knee is extended and also over a range of flexion. The condyles are in the form of respective parts of two adjacent helices (each having a common pitch) and the respective matching surfaces of the bearing component are correspondingly part-helical. Although this design represents an improvement over the above and provides a high level of congruity at the femoro-meniscal joint, the design also requires that the bearing component is mobile with respect to the tibial component so as to allow for rotation of the knee and this can have attendant drawbacks in terms of complexity of design and surgical implantation as well as cost.

Further, where non-congruent medial and lateral condyle and respective bearing surfaces are provided, there is a possibility that the femoral component may displace relative to the tibial component, which can lead to instability of the knee joint at low flexion.

An object of the present invention is therefore to provide an improved knee prosthesis which reduces or obviates at least one of the disadvantages of the prior art, or provides a useful alternative.

SUMMARY OF THE INVENTION

According to aspects of the invention, there is provided a knee prosthesis comprising a femoral component for securement to a femur. The femoral component may define medial and lateral condyles and an intercondylar groove. Further, in aspects of the invention, a tibial component is provided for securement to a tibia. The tibial component may comprise respective bearing surfaces shaped to engage with said condyles both when the knee, in use, is extended and also over a range of flexion.

The femoral and tibial components together may comprise interengaging means. These interengaging means may be for stabilising the prosthesis against antero-posterior relative movement of the femoral and tibial components at flexion above a first predetermined angle. One of the condyles and the respective bearing surface of the tibial component may be congruent, at least in a plane extending through a contact line of said one condyle and the respective bearing surface, at angles of flexion below a second predetermined angle. The one condyle may be completely congruent with the respective bearing surface at the low angles of flexion, while it may be only along the contact line, for example where a sagittal radius of the femoral condyle is different from the transverse radius at the low angles of flexion, and the respective bearing surface is part spherical with a radius substantially equal to the larger of the sagittal and transverse radii of the condyle. The contact line may therefore rotate as the condyle rotates within the tibial bearing surface. The other bearing surface may be incongruent with the other condyle in at least the antero-posterior direction at all angles of flexion so as to allow for antero-posterior movement of the femoral component relative to the bearing surfaces of the tibial component.

The interengaging means may comprise a peg and cooperating cam or a ball and socket. The cooperating cam (or ball) may be formed in the region of the intercondylar groove of the femoral component and the peg (or socket) is formed projecting from the tibial component. The cam (or ball) may extend across the intercondylar groove from the medial side to the lateral side of the prosthesis at the back of an intercondylar box. A surface of the peg (or socket) which engages with the cam (or ball) may be rounded so as to allow the surface of the cam (or ball) to rotate about the peg (or socket) in a plane substantially parallel to a notional plane passing through both bearing surfaces of the tibial component.

The knee prosthesis may be rotatable from a first position in which said one condyle and respective bearing surface are congruent to a second position in which said one condyle and corresponding bearing surface become incongruent, the cam and peg may engage on rotation of the knee prosthesis after leaving the first position, and before, when or after reaching the second position. The first predetermined angle may be in a range between approximately 50 and 120 degrees. Alternatively, the first predetermined angle may be in the range between 60 and 110 degrees, or 60 and 100 degrees, 60 and 80 degrees, or around 50, 60, 70, 80, 90, 100, 110, 120, or 130 degrees. The second predetermined angle may be in a range between approximately 50 and 120 degrees, 70 and 110 degrees, 80 and 100 degrees, or around 50, 60, 70, 80, 90, 100, 110, 120, or 130 degrees for example.

The medial condyle and corresponding bearing surface may be congruent at least at angles of flexion below the second predetermined angle. The surface of the medial condyle and corresponding bearing surface may be rounded with equal radius in both the flexion and extension facets of the prosthesis. Alternatively, the lateral condyle and bearing surface may be congruent, at least at low flexion angles, and the medial condyle and bearing surface incongruent.

In this way, a prosthesis which provides antero-posterior stability at low flexion angles can be formed by use of the medial (lateral) congruence between condyle and bearing surface to provide a rotation axis substantially parallel to the tibia, in use, to form a medial rotating joint. Further, in the same prosthesis, high flexion stability can be formed by use of engaging cam and follower which engage at high flexion and push the femoral component posteriorly relative to the tibial component and minimise relative antero-posterior movement of the femeral and tibial components to form a posteriorly stabilised joint.

According to another aspect of the present invention there is provided a knee prosthesis. The prosthesis may comprise a femoral component for securement to a femur, the femoral component defining medial and lateral condyles and an intercondylar groove, and may also comprise a tibial component for securement to a tibia, the tibial component having respective bearing surfaces shaped to engage with said condyles both when the knee, in use, is extended and also over a range of flexion. At least one of the condyles may be part-helical in shape and the respective bearing surface of the tibial component being correspondingly part-helical in at least a medio-lateral direction. The other bearing surface may be incongruent with the other condyle in at least the antero-posterior direction so as to allow for antero-posterior movement of the femoral component relative to the bearing surfaces of the tibial component.

Embodiments of the present invention therefore provide a knee prosthesis which, due to the presence of at least one helical condyle rotating in a medio-lateral conforming bearing surface, provides the desired lateral translation of the intercondylar groove when the knee is flexed, therefore ensuring correct patellar tracking. However, unlike in GB2387546B, the present design does not require a mobile bearing component in order to allow rotation of the knee. Instead, the present knee prosthesis includes bearing surfaces which are fixed with respect to the tibial component and wherein the required antero-posterior movement is permitted by the incongruent nature of the other condyle. The fixed bearing therefore negates the complexities of implanting a mobile bearing design, as in the prior art, whilst retaining the advantages of correct patella tracking.

However, it is not possible to have a fixed bearing design with highly conforming congruent bearing surfaces which match helical condyles on both the lateral and medial side since the knee would not be permitted to rotate and such a design would generate forces that would loosen the components. Thus, instead of a mobile bearing with congruent contact between the femoral component and the meniscus bearing component, the present invention provides a fixed bearing, without a separate meniscal component, and incongruent contact between the femoral component and the tibial component.

Flexion of the knee, in use, from an extended position may induce lateral translatory movement of the femoral component upon the tibial component. The lateral translatory movement may be 3.5 mm per 90° of flexion.

In certain embodiments, at least one of the condyles may have point or line contact, as opposed to area contact, with a respective bearing surface.

At least the bearing surfaces of the tibial component may comprise a polymer, preferably a cross-linked polymer. For example, the bearing surfaces may comprise polyethylene, preferably, UHMWPE and, more preferably, cross-linked UHMWPE. The tibial bearing surface may comprise a hybrid polyethylene component where the bulk of the component is conventional polyethylene to retain strength and the bearing surface only is cross-linked polyethylene to give wear resistance as disclosed in GB2387546B. The lack of area contact between the femoral component and the tibial component can therefore be compensated for by improved wear characteristics arising from cross-linking of the bearing surfaces.

The at least one condyle may be shaped in the manner of the threads on a screw, and the respective bearing surface may be shaped in the manner of threads cut in a complementary nut. However, the respective bearing surface could be in the manner of the threads on the screw, with the at least one condyle shaped in the manner of the threads cut in the nut.

The medial and lateral condyles may have the same shapes or may be differently shaped. For example, the medial and lateral condyles may both be part-helical in shape (e.g. the condyles may be in the form of respective parts of two adjacent helices, which may or may not have a common pitch). Alternatively, one condyle may be non-helical.

In particular embodiments, at least the medial condyle is part-helical in shape.

In a specific embodiment, the knee prosthesis may be configured as a medially pivoting knee. In which case, the medial condyle is part-helical in shape and is configured for congruent (area) contact with a respective bearing surface which is correspondingly part-helical in both the medio-lateral direction and the antero-posterior direction. The lateral condyle in this embodiment may also be part-helical. In which case, the respective bearing surface for the lateral condyle will be configured for incongruent (line or point) contact and may be part-helical in the medio-lateral direction only (i.e. to form a trough) or may be planar or curved. Alternatively, the lateral condyle may be non-helical and the respective bearing surface may be planar or curved and may be configured for incongruent contact in both the antero-posterior direction and the medio-lateral direction. It will be understood that the incongruent contact between the lateral condyle and the respective bearing surface allows the required antero-posterior movement of the femoral component upon rotation of the knee. In this particular embodiment, the femoral component is allowed to rotate around the medial femoro-tibial articulation with antero-posterior movement at the lateral femoro-tibial articulation. The reverse arrangement is also possible with a helical near conforming lateral femoro-tibial articulation providing desirable lateral femoral translation with increasing knee flexion and rotation being allowed for with an incongruent medial femoro-tibial articulation giving antero-posterior movement.

In another embodiment, the knee prosthesis may be configured as a so-called Total Condylar Design such that the intact posterior cruciate ligament causes roll-back of the femoral component on the tibial component with increasing flexion. In this case, the medial condyle, the lateral condyle or both condyles may be part helical in shape. However, unlike for the above embodiment, in this case, each of the bearing surfaces must be configured for incongruent contact with the respective condyles in the antero-posterior direction so as to allow for the femoral component to freely slide back and forth on the tibial component during flexion and extension. It will be understood that any constraint in the antero-posterior direction as a result of the shapes of the bearing surfaces, will cause conflict with the movement dictated by the posterior cruciate ligament with resultant component loosening and/or component breakage, hence the need for complete incongruent contact in the antero-posterior direction, in this embodiment. However, in order to ensure that lateral translation of the intercondylar groove is maintained, at least one of the condyles must be part-helical and the respective bearing surface of the tibial component must be correspondingly part-helical in the medio-lateral direction only (i.e. the respective bearing surface should be in the form of a trough, giving side-to-side conformity and normal translation, but offering no front-to-back constraint). A single part-helical condyle articulating in such a medio-laterally constrained bearing surface is believed to be sufficient to provide the desired lateral translation.

As above, the other condyle in this embodiment may either be part-helical or non-helical. If the other condyle is part-helical the respective bearing surface may or may not be similarly helical in the medio-lateral direction. If the other femoral condyle is non-helical, the respective bearing surface must not constrain the movement of the other condyle in the medio-lateral direction since any such constraint would result in a conflict which would likely result in breakage or severe wear. For example, the helical condyle in its medio-laterally constrained trough will try to cause lateral translation, but if the non-helical other condyle is also constrained medio-laterally it will try to prevent any lateral translation.

In another embodiment, the knee prosthesis may be configured as a so-called Posterior Stabilised Design where there is no functioning posterior cruciate ligament but, at increasing flexion (e.g. at approximately 80 degrees of flexion, i.e. between 75-90 degrees), a peg and cam (or ball and socket) mechanism are designed to engage to cause roll-back of the femoral component on the tibial component. Thus, the condyles and bearing surfaces must essentially be designed as per the Total Condylar Design described above so as to ensure that there is no constraint on antero-posterior movement when the peg and cam (or ball and socket) are engaged. In such embodiments, the knee prosthesis may be configured substantially in line with the applicants' earlier GB2426201 with the condyles and bearing surfaces being adapted in line with the present invention. Again at least one femoral condyle is part helical with medio-lateral engagement with its respective tibial bearing surface to generate desirable femoral translation with knee flexion.

The transverse cross-section of each condyle may be flat, curved or semi-spherical and may be the same or different for each condyle.

The tibial component may be constituted by a single component, which may be all polyethylene, or a multi-part component. For example, the tibial component may comprise a bearing component comprising the bearing surfaces and an engaging (tibial baseplate) component comprising an engagement feature for securing the tibial component to a patient's tibia. The bearing component may be configured for snap-fit engagement with the engaging component, or may be manufactured fitted to the tibial baseplate. The bearing component may be formed from a polymer, preferably a cross-linked polymer. For example, bearing component may be formed from polyethylene, preferably, UHMWPE and, more preferably, cross-linked UHMWPE, and more preferably hybrid polyethylene. The tibial baseplate may commonly be formed from a metal, but could also be formed from a tough polymer such as PEEK (polyether ether ketone). For example, engaging component may be formed from polyethylene, preferably, UHMWPE and, more preferably, cross-linked UHMWPE. Alternatively, the engaging component may be formed from metal.

In accordance with another aspect of the invention, there is provided a knee prosthesis comprising:
- a femoral component for securement to a femur, the femoral component defining medial and lateral J-shaped condyles and an intercondylar groove; and
- a fixed bearing tibial component for securement to a tibia, the tibial component having respective bearing surfaces which are fixed with respect to both a tibial engaging component and a stabilising peg for securing the tibial component to a tibia, the respective bearing surfaces being shaped to engage with said condyles both when the knee, in use, is extended and also over a range of flexion, wherein:
- the femoral and tibial components together comprise interengaging features, for stabilising against antero-posterior relative movement of the femoral and tibial components at flexion above a first predetermined angle of 110 degrees, wherein both the medial and lateral condyles are incongruent and unconstrained in an antero-posterior direction with the respective bearing surfaces at angles of flexion above the first predetermined angle of 110 degrees to allow for roll-back of the femoral component relative to the bearing surfaces, tibial engaging component, and stabilising peg;
- one of the condyles and the respective bearing surface of the tibial component are congruent at angles of flexion below a second predetermined angle of at least 70 degrees;
- the other bearing surface is incongruent with the other condyle in at least the antero-posterior direction at angles of flexion below the second predetermined angle of at least 70 degrees, so as to allow for antero-posterior movement of the femoral component relative to the bearing surfaces of the tibial component; and
- wherein a transition zone is provided at angles of flexion between the second and first predetermined angles, in the transition zone the interengaging features begin to contact and the one condyle becomes incongruent from a posterior to an anterior of the respective bearing surface, which encourages external rotation and posterior translation of the other condyle until the first predetermined angle is reached, wherein both internal and external rotation is permitted.

The interengaging features may comprise a peg and cooperating cam or a ball and socket.

In some embodiments, the interengaging features may have a centre of rotation that is co-axial with a centre of rotation of a posterior radius of at least one condyle.

The cam or ball may be formed in the region of the intercondylar groove of the femoral component and the peg or socket may be formed in or projecting from the tibial component.

The cam or ball may extend across the intercondylar groove from the medial side to the lateral side of the prosthesis.

A surface of the peg/socket which engages with the cam/ball may be rounded so as to allow the surface of the cam/ball to rotate about the peg/socket in a plane substantially parallel to a notional plane passing through both bearing surfaces of the tibial component.

The knee prosthesis may be rotatable from a first position in which said one condyle and respective bearing surface are congruent to a second position in which said one condyle and respective bearing surface become incongruent, the cam/ball and peg/socket engaging on rotation of the knee prosthesis after leaving the first position, and before reaching the second position.

The second predetermined angle may be in a range between approximately 70 and 100 degrees.

The medial condyle and corresponding bearing surface may be congruent at angles of flexion below the second predetermined angle.

A surface of the medial condyle and corresponding bearing surface may be rounded with equal radius in both flexion and extension facets of the prosthesis.

At least one of the condyles may have point or line contact, as opposed to area contact, with a respective bearing surface.

At least one of the condyles may be part-helical in shape and the respective bearing surface of the tibial component being correspondingly part-helical in at least a medio-lateral direction.

At least the bearing surfaces of the tibial component may comprise a cross-linked polymer.

The condyles may be shaped in the manner of the threads on a screw, and the respective bearing surface may be shaped in the manner of threads cut in a complementary nut.

At least one of the medial and lateral condyles may be part-helical in shape.

The other condyle may be non-helical.

The medial condyle may be part-helical in shape and configured for congruent contact with a respective bearing surface which is correspondingly part-helical in both the medio-lateral direction and the antero-posterior direction.

The lateral condyle may be part-helical in shape and the respective bearing surface for the lateral condyle may be configured for incongruent contact in at least the antero-posterior direction.

The lateral condyle may be non-helical and the respective bearing surface may be configured for incongruent contact in both the antero-posterior direction and the medio-lateral direction.

The transverse cross-section of one condyle may be flat, curved or semi-spherical.

The transverse cross-section may be different for each condyle.

BRIEF DESCRIPTION OF THE DRAWINGS

The invention will now be described, by way of example, with reference to the accompanying drawings, in which:

FIGS. 22a to 22h show various elevations and cross-sections trough the tibial component of a prosthesis according to an embodiment of the invention;

FIGS. 23a and 23b show rotation of the femoral component relative to the tibial component of a knee prosthesis according to an embodiment of the invention at a flexion angle of around 120 degrees;

FIGS. 24a and 24b show rotation of the femoral component relative to the tibial component of a knee prosthesis according to an embodiment of the invention at a flexion angle of around 30 degrees;

FIGS. 25a and 25b show a knee prosthesis according to an embodiment of the invention, and cross section through the knee prosthesis;

FIGS. 32a, b and c show respectively a front, side and top view of a prosthesis similar to that of FIG. 28a at 85 degrees of flexion and FIGS. 32d, e and f show respectively cross-sectional views along lines AA, BB and FF shown in FIG. 32a; and FIGS. 33a, b and c show respectively a front, side and top view of a prosthesis similar to that of FIG. 28a at 140 degrees of flexion and FIGS. 33d, e and f show respectively cross-sectional views along lines AA, BB and FF shown in FIG. 33a.

DETAILED DESCRIPTION OF SPECIFIC EMBODIMENTS

As will be described in relation to the knee prosthesis shown in the accompanying Figures, embodiments of the present invention generally relate to the shaping of at least one of the medial and lateral condyles and the engagement with a corresponding bearing surface of the tibial component, for example in the manner of a screw-thread and associated corresponding nut engaged therewith. Although it would be possible to provide condyles in the form of the threads cut in the nut, with the threads on the screw being provided by the bearing surfaces, it is preferred, as will be described, that the screw-threads, i.e. the male part of the thread will be defined by the at least one condyle, with the bearing surface being correspondingly grooved in the nature of the threads cut in the nut. By this means, as will be more fully explained below, lateral translation of the femoral component can be realised without requiring a mobile bearing component to accommodate antero-posterior movement as the knee is flexed.

Figure 1:
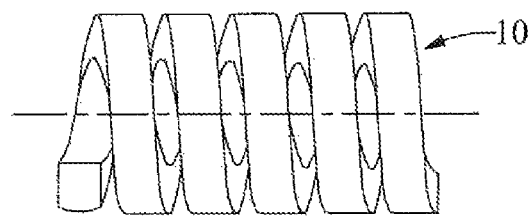
FIGS. 1 to 3 are schematic explanatory views relating to the formation of one or more helical condyles of a femoral component of a knee prosthesis according to embodiments of the present invention.
Figure 2:
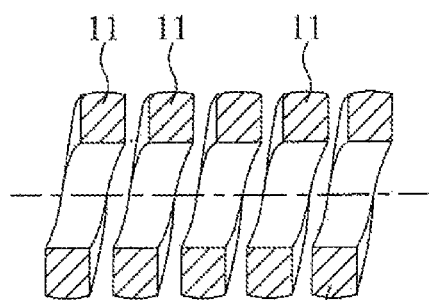

FIGS. 1 to 4A schematically show the form of the helical nature of the femoral condyles and the grooves in a tibial bearing component according to an embodiment of the invention. FIG. 1 shows a helix 10 with a certain selected angle defining the pitch of the thread. FIG. 2 shows a section through the helix of FIG. 1 so as to define a series of spaced part-helical forms 11. It will be understood how two of these can be adapted to form the shape of the respective sections 12, 13 shown in FIG. 3 which approximate to the condylar sections of a femoral component to be described in relation to the drawings showing the assembled prosthesis. However, it will also be understood that embodiments of the present invention may include only one such helical condyle 12, 13 with the other condyle being non-helical, for example, circular.

Medial Rotating Design

Figure 4A:
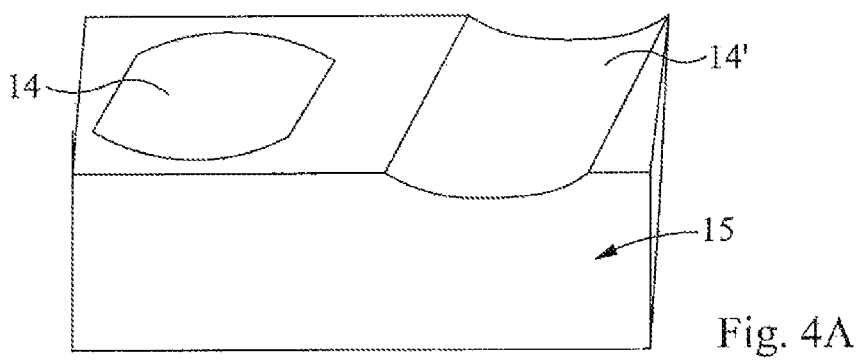
FIGS. 4A and 4B are further schematic, explanatory views showing the formation of part-helical grooves constituting bearing surfaces of a tibial component for a knee prosthesis according to embodiments of the present invention.
Figure 10C:
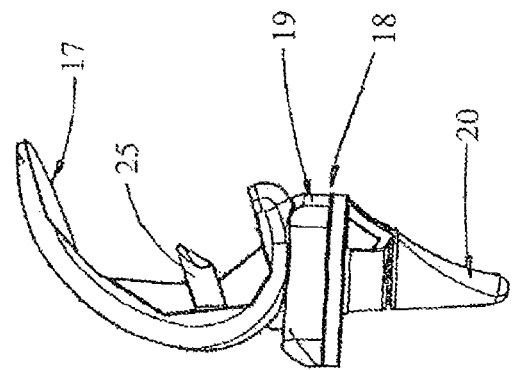
FIGS. 10A to 10C show respectively, a front, medial side and lateral side view of a prosthesis according to an embodiment of the present invention, with the knee in a partly flexed state.

A further illustration of the nature of the part-helical arrangement of a prosthesis according to an embodiment of the present invention is shown in FIG. 4A in relation to the shapes of the respective grooves or bearing surfaces 14, 14' formed in the tibial component which is schematically shown in the form of a block 15. It can be seen that each groove is at an angle to the longitudinal extent of the block, this angle corresponding to the angle of the helix 10 shown in FIG. 10, with the two part-helical sections 12, 13 of the helix 10 corresponding respectively in at least the (transverse) medio-lateral direction with the grooves 14, 14' of the tibial component. More specifically, the medial bearing surface 14 is shaped to conform exactly with the medial condyle 12 so as to produce congruent area contact in both the medio-lateral direction and the antero-posterior direction (i.e. the surface 14 is curved both side-to-side and front-to-back). On the other hand, the lateral bearing surface 14' is shaped only to conform with the lateral condyle 13 in the medio-lateral direction so as to produce incongruent line contact (i.e. the surface 14' is curved side-to-side but straight front-to-back). It will be understood that such a configuration will allow a femoral component comprising the condyles 12, 13 to rotate on the tibial component 15, thereby permitting antero-posterior movement when the condyles 12, 13 are engaged in the bearing surfaces 14, 14'.

Figure 4B:
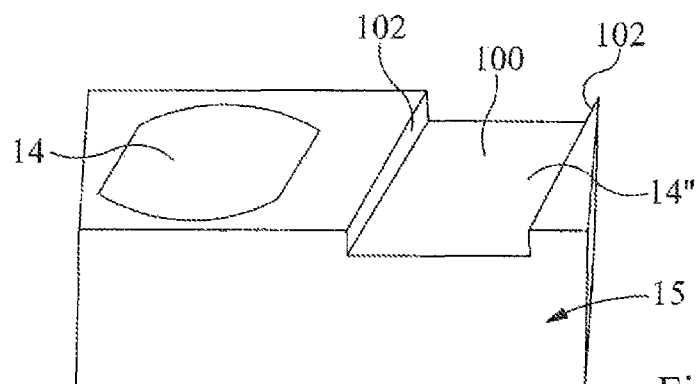

FIG. 4B shows an alternative schematic tibial component 15 in which the medial bearing surface 14 is the same as in FIG. 4A but wherein the groove constituting the lateral bearing surface 14" has been squared off to comprise a flat base 100 and two opposed perpendicular side walls 102. However, the angle of the groove 14" has not been altered and is consistent with both the angle of the groove 14 and the angle of each of the part-helical condyles 12, 13. Since the condyles 12, 13 have a curved transverse cross-section, in this embodiment, the lateral condyle 13 will only make point contact with the base 100 of groove 14". However, as above, antero-posterior movement of the femoral component is permitted since there is no antero-posterior constraint imposed on the lateral condyle 13 by the surface 14".

Figure 3:
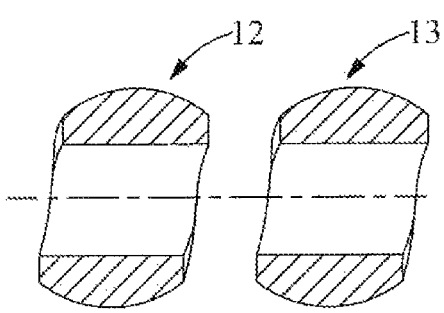
Figure 5:
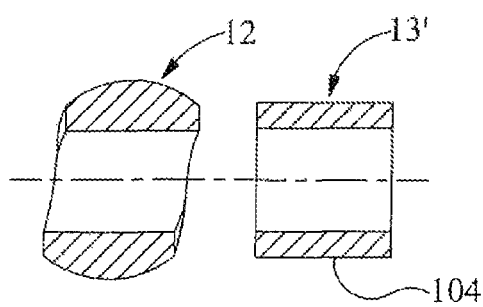
FIG. 5 is view similar to that of FIG. 3 but wherein only one condyle is part-helical and the other condyle is circular, having a flat engagement surface in accordance with an embodiment of the present invention.

FIG. 5 shows a view similar to that of FIG. 3 but wherein only one condyle 12 is part-helical and the other condyle 13' is circular, having a flat engagement surface 104 in accordance with an embodiment of the present invention.

Figure 6:
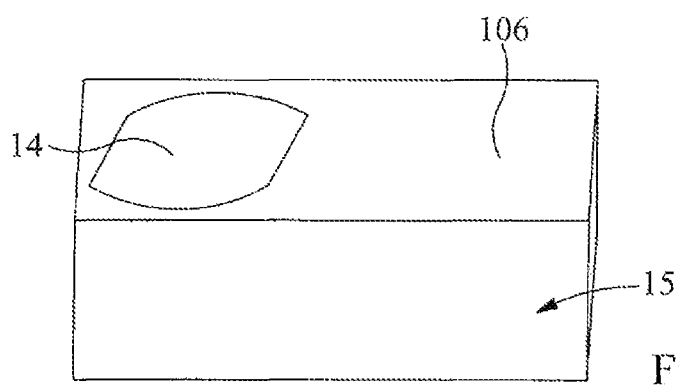
FIGS. 6 to 9 are further schematic, explanatory views showing the formation of various bearing surfaces of a tibial component for a knee prosthesis according to embodiments of the present invention.

FIG. 6 shows a further schematic tibial component 15 which has been configured for use with the condyles 12, 13' of FIG. 5. Thus, tibial component 15 comprises a medial bearing surface 14 which is the same as in FIGS. 4A and 4B but wherein no groove is provided on the lateral side and, instead, the lateral side of the tibial component 15 has a planar surface constituting a lateral bearing surface 106 for engagement with the lateral condyle 13'. It will be understood that, when the condyles 12, 13' of FIG. 5 are engaged with the tibial component 15 of FIG. 6, area contact will be achieved on the medial side and line contact will be achieved on the lateral side. Furthermore, the helical medial condyle 12 will induce a lateral translation of the femoral component while the lateral condyle 13' will be allowed to move in an antero-posterior direction to permit rotation of the femoral component with respect to the tibial component 15.

Total Condylar Design

Figure 7:
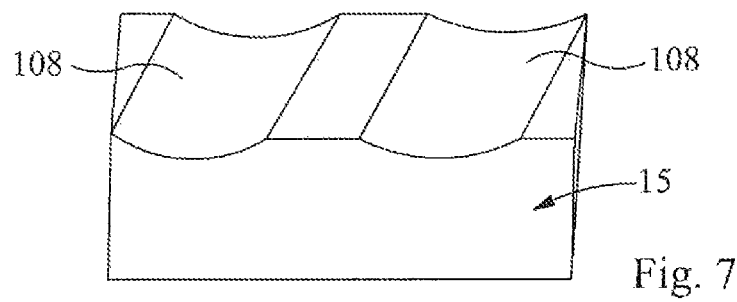

FIG. 7 shows a further schematic tibial component 15 which has been configured for use with the condyles 12, 13 of FIG. 3 in accordance with another embodiment of the invention. In this case, each of the grooves 108 constituting the bearing surfaces are configured as per the lateral bearing surface 14' of FIG. 4A. Thus, the bearing surfaces 108 are shaped only to conform with the lateral condyle 13 in the medio-lateral direction so as to produce incongruent line contact (i.e. the surfaces 108 are curved side-to-side but straight, albeit angled, front-to-back). This embodiment, therefore allows each condyle to move in an antero-posterior direction upon knee rotation, for example, so as to allow for the action of an intact posterior cruciate ligament pulling the femoral component backwards as the knee is flexed.

Figure 8:
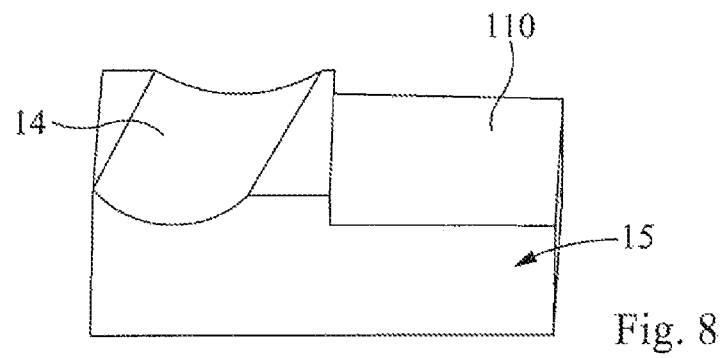

FIG. 8 shows another schematic tibial component 15, which is similar to that in FIG. 7 but wherein the top portion of the lateral side of the tibial component 15 has been removed to form a sunken planar bearing surface 110. As above, this tibial component 15 may be used alongside the condyles 12, 13 of FIG. 3 such that the medial condyle 12 causes lateral translation of the femoral component and both the medial and lateral condyles 12, 13 are free to move in an antero-posterior direction.

Figure 9:
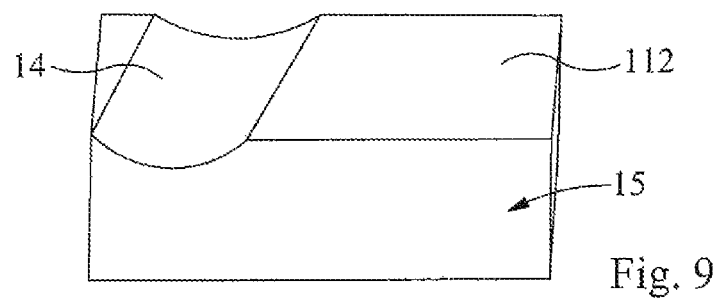

FIG. 9 shows a still further schematic tibial component 15, which is similar to that in FIG. 8 but wherein the top portion of the lateral side of the tibial component 15 is maintained and is formed into a planar bearing surface 112 similar to that of FIG. 6. Accordingly, this tibial component 15 may be used with the condyles 12, 13' of FIG. 5 in a similar manner to that described above in relation to FIG. 8.

Figure 10A:
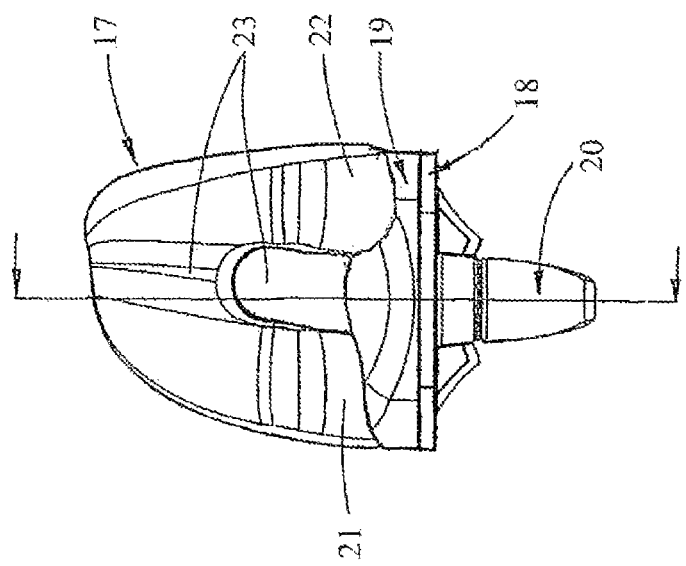
Figure 10B:
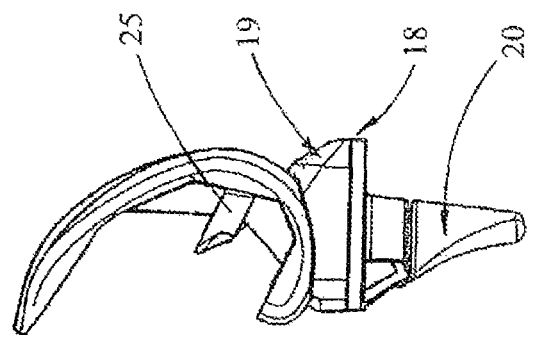
Figure 11A:
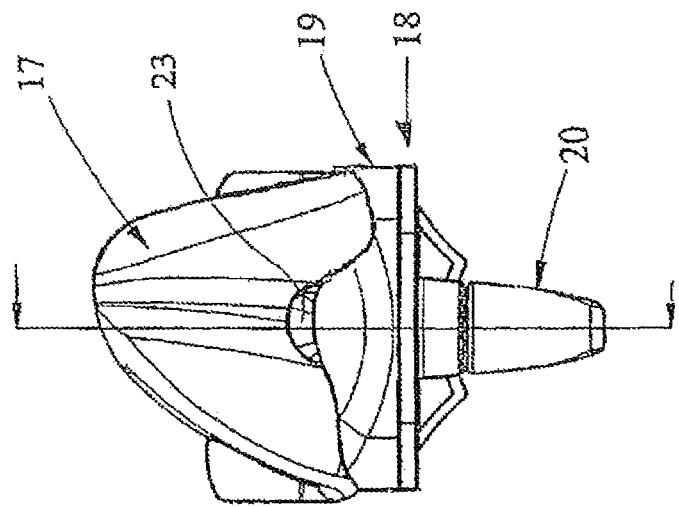
FIGS. 11A and 11B show respectively, a front and medial side view of the prosthesis of FIGS. 10A through 10C, with the knee in an extended state.
Figure 11B:
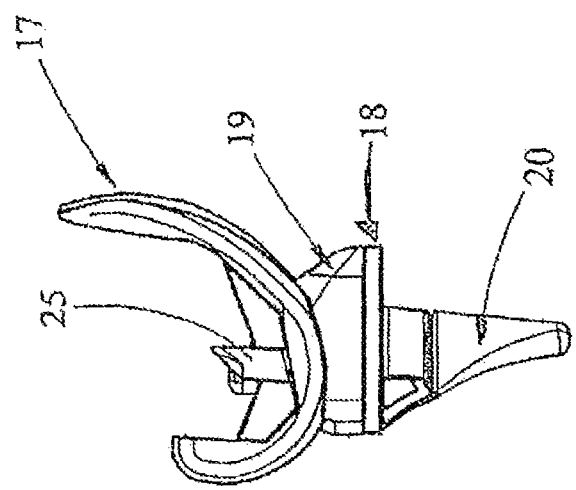

FIGS. 10A through 11B show an assembled prosthesis comprising a femoral component 17 and a tibial component 18. The tibial component 18 is comprised of a fixed bearing component 19 disposed on an engaging component in the form of a stabilising peg 20. It is intended that in use the femoral component 17 is secured to the end of the femur from which bone has appropriately been removed. The femoral component 17 can be fixed in any suitable manner. The peg 20 is, in use, secured to the top of the tibia, again in any suitable manner. Whilst FIGS. 10A to 10C show the prosthesis in a state equivalent to one fitted to a partly flexed knee, FIGS. 11A and 11B show the state when it is fitted to a knee which is extended.

Figure 12C:
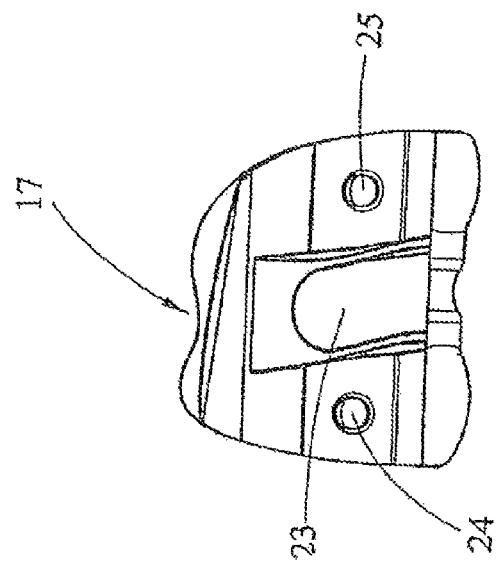
FIGS. 12A to 12C show respectively a front, side and rear view of a femoral component of a knee prosthesis according to embodiments of the present invention.
Figure 12B:
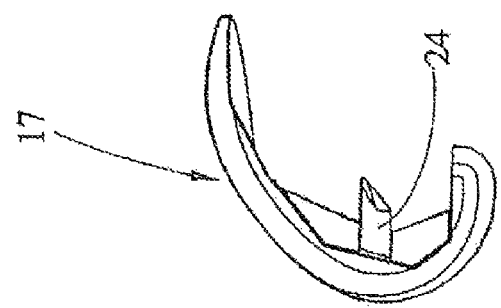
Figure 12A:
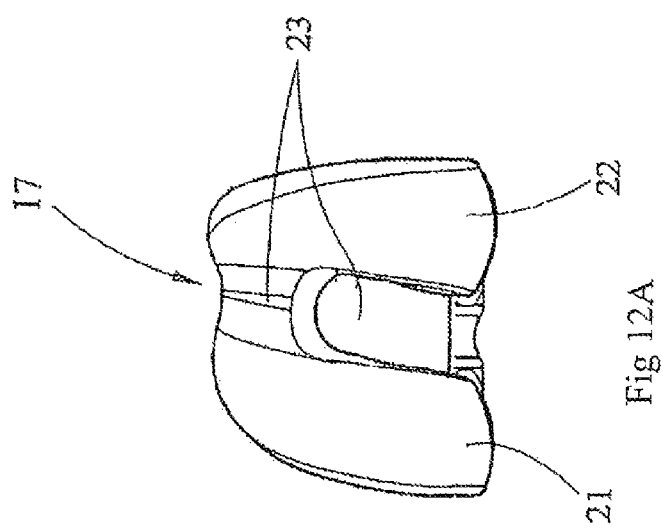

The femoral component 17 is shown in more detail in FIGS. 12A through 12C and is of a generally known form defining outer generally arcuate medial condylar and lateral condylar surfaces 21, 22 respectively. In this embodiment, the condyles 21, 22 are shaped similarly to those shown in FIG. 3, in the manner of screw-threads, i.e. are each part-helical, being formed from the same helix. Defined between and parallel to the medial and lateral condyles is the intercondylar (patella) groove 23. From FIGS. 10A and 11A, for example, it will be appreciated that the helical nature of the condyles 21, 22 results in the patellar-femoral articulation being displaced laterally with respect to the mid-point of the tibial-femoral articulation as the knee rotates. The patella groove is thus laterally displaced, the amount of lateral displacement depending upon the pitch of the 'threads' which the condyles define.

From FIGS. 12B and 12C it can be seen that at the interior surface of the femoral component 17, at respective opposite sides of the patella groove are respective pegs 24, 25 to facilitate fixing of the femoral component 17 to the end of the femur, in use.

Figure 13A:
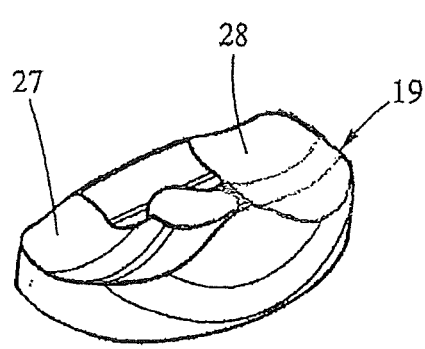
FIGS. 13A to 13C show respectively a perspective, plan and side view of a bearing component of a tibial component of a knee prosthesis according to embodiments of the present invention.
Figure 13B:
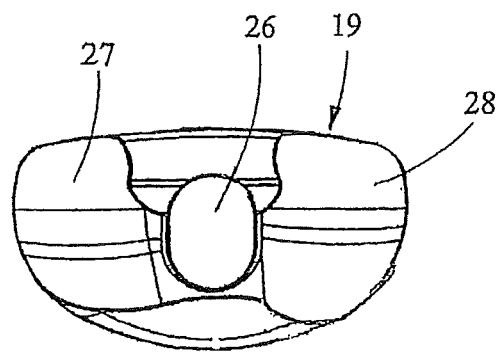
Figure 13C:

FIGS. 13A to 13C show the bearing component 19, which has a raised central area 26 between bearing surfaces 27, 28. In this particular embodiment, the bearing surfaces 27, 28 are similar to those of FIG. 4A in that the medial bearing surface 27 is shaped to conform exactly with the medial condyle 21 so as to produce congruent area contact in both the medio-lateral direction and the antero-posterior direction while the lateral bearing surface 28 is shaped only to conform with the lateral condyle 22 in the medio-lateral direction so as to produce incongruent line contact and to allow antero-posterior movement. In other embodiments, the bearing surfaces may be configured as per those shown in the other schematic illustrations of the tibial component 15.

Figure 14A:
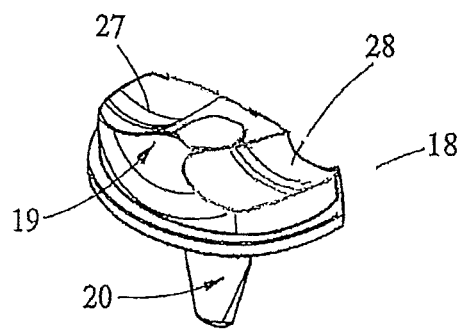
FIGS. 14A to 14C show respectively a perspective, front and plan view of a tibial component including the bearing component of FIGS. 13A to 13C.
Figure 14B:
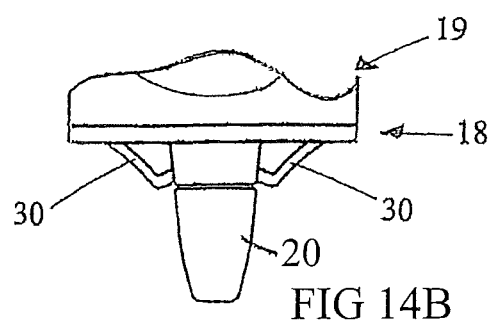
Figure 14C:
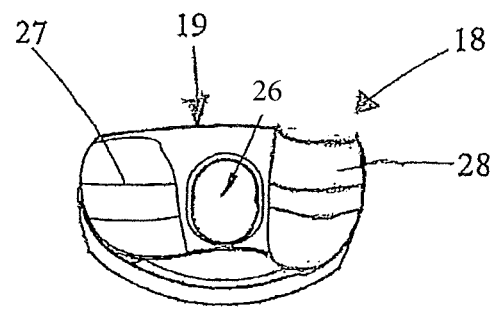

As shown in FIGS. 14A through 14C, the bearing component 19 is snap-fitted onto the engaging component and the peg 20 is provided with ribs 30 to assist fixing of the tibial component 18 to the tibia, in use.

It will be appreciated that the femoral component 17 would normally be of metallic material with its condylar surfaces 21, 22 highly polished. Typically, it could be of cobalt chrome and would be affixed to the femur by any form of suitable cement adhesion or biological fixation. Similarly, the engaging component 20 would also normally be of metallic material, again such as cobalt chrome. However, the bearing component 19 preferably comprises cross-linked Ultra High Molecular Weight Polyethylene (UHMPE) at least for its bearing surfaces 27, 28.

It is believed that it will be appreciated from the above, in conjunction with FIGS. 10A through 11B how the prosthesis of the present embodiment operates, in use.

As described above, the helical form of at least one of the condyles of the femoral component serves to displace the patella groove laterally. This is a static effect, with the amount of lateral displacement being proportional to the angle of the helix. Additionally, the helical arrangement means that the 'helix' advances when turned relative to the bearing component 19. Accordingly when the knee is flexed, in use, from an extended position, the helical nature of the at least one condyle induces a lateral translatory movement of the femoral component, and thus of the femur, upon the tibial component 18. This is a dynamic effect corresponding to the turning of a thread relative to a fixed nut. This again is desirable because the whole of the femur, and thus the patella groove also, is moved laterally with increasing flexion of the knee. However, it also a feature of the present invention that at least one of the condyles is unconstrained in at least an antero-posterior direction. This allows the femoral component to shift backwards with respect to the tibial component and, in some embodiments, allows rotation of the femoral component around the tibial axis, without the need for a rotating platform design as in the prior art.

Figure 15A:
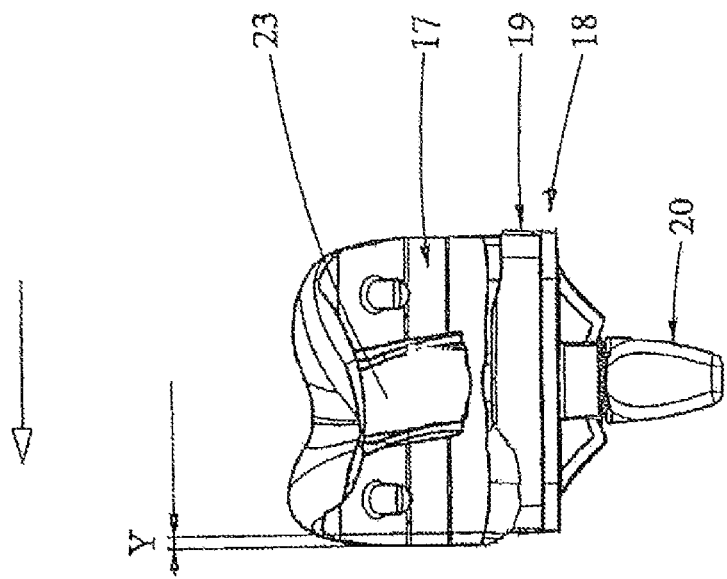
FIGS. 15A and 15B show respective rear views of a prosthesis in accordance with an embodiment of the present invention, in both fully extended and fully flexed states of the knee.
Figure 15B:
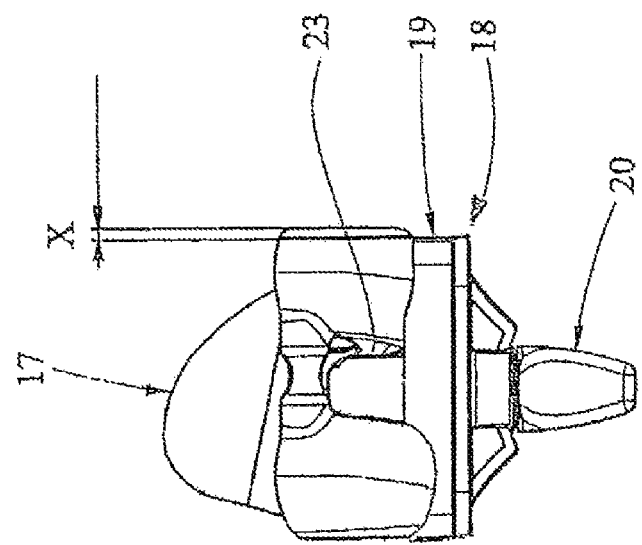

FIGS. 15A and 15B show the assembled knee prosthesis in fully extended and fully flexed states of the knee, in use. Typically, there is lateral translatory movement of the femur upon the tibia to the extent shown, i.e. with a lateral shift of 3.5 mm per 90°. These Figures show the respective overhangs X and Y at the respective opposite sides of the prosthesis in the fully extended and fully flexed states respectively.

Posterior Stabilised Design

Figure 16:
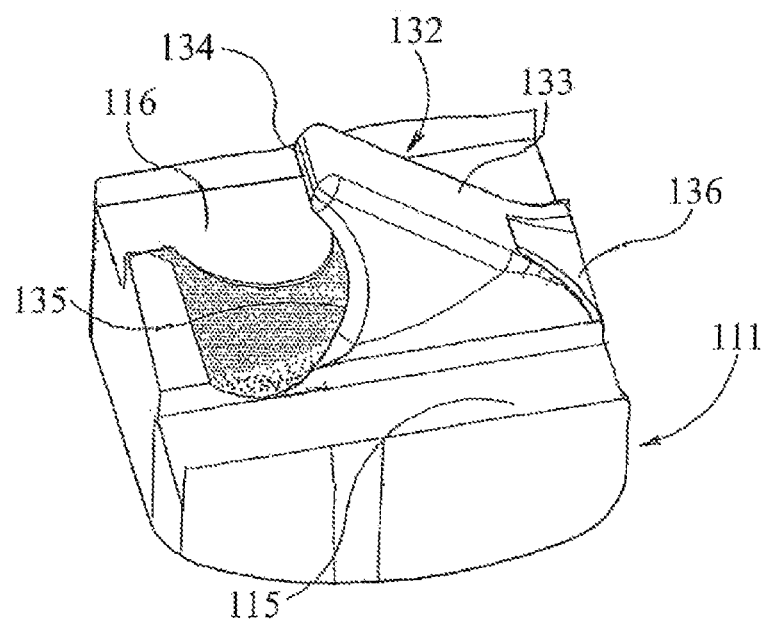
FIG. 16 shows a rear perspective view of another bearing component of a tibial component of a knee prosthesis according to embodiments of the present invention.
Figure 17:
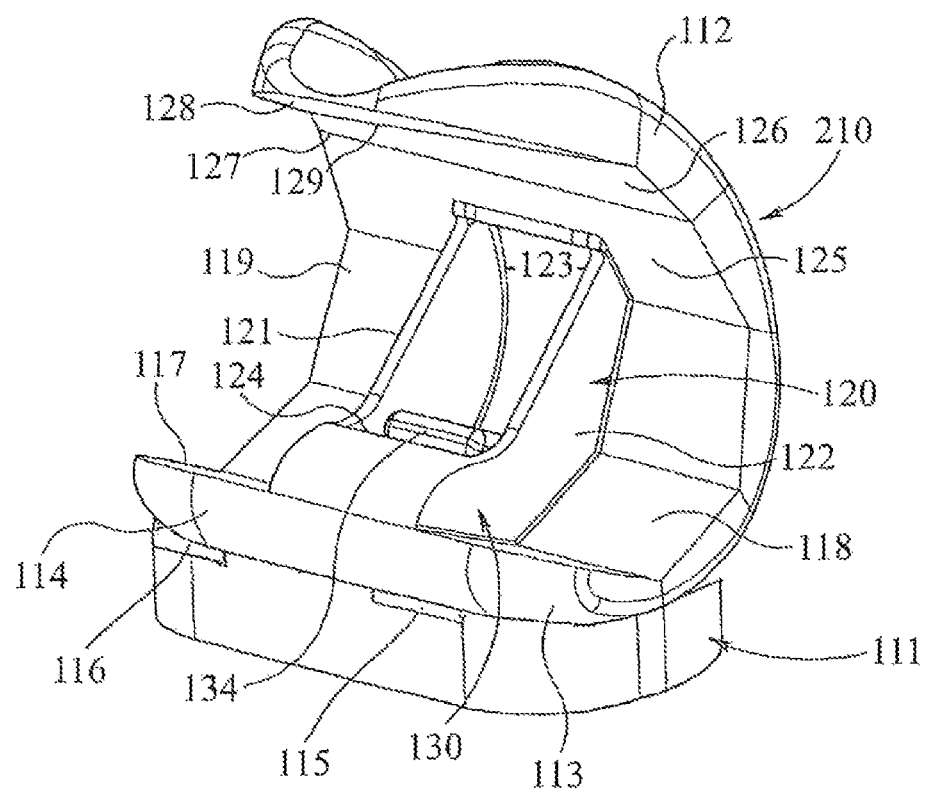
FIG. 17 shows a rear perspective view of the bearing component of FIG. 16 when engaged (via a cam and peg mechanism) with a femoral component for a knee prosthesis according to an embodiment of the present invention.

FIG. 16 shows a rear view of another bearing component 111 of a tibial component of a knee prosthesis according to another embodiment of the present invention and FIG. 17 shows a rear view of the bearing component 111 of FIG. 16 when engaged (via a cam 130 and peg 132 mechanism) with a femoral component 210.

The bearing component 111 has medial and lateral bearing surfaces 115, 116 which are similar in form to those illustrated in FIG. 7 but which are each squared off to forms angled troughs having a base and two perpendicular sidewalls. Thus, the bearing surfaces 115, 116 are configured to constrain helical condyles only in a medio-lateral direction and to allow unconstrained movement in an antero-posterior direction.

Centrally of the component 111, but towards the slightly convex front peripheral side surface thereof is formed an upstanding peg 132, constituting a follower, with the opposite rear peripheral side surface of the bearing component being flat, with the peg 32 terminating short thereof.

As can be seen from FIG. 16, the peg 132 has a body which rises with an upwardly angled flat top surface 133 from the front side surface to form an arcuate downwardly extending front nose part 134. Below this part 134 is a cam follower surface constituted by a recess 135 which is of part-cylindrical concave form to match a cylindrical external surface of a cam 130 of the femoral component 210 so that, as will be described, cam 130 can engage in the recess 135 and follow the shape of the recess thereby allowing the femoral component 210 to move relative to the bearing component 111 during flexion of the knee. The recess 135 extends through approximately 180° from the surface of the bearing component 111 between the bearing surfaces 115, 116 to the lower edge of the front part 134. However the angle through which the recess 135 extends can be varied as required, and the respective shapes of the inter-engaging parts of the cam 130 and the follower (peg 132) can also be varied as required. In the embodiment illustrated, there is also provided a lateralised recess 136 at the front side of the component 111 to accommodate a lateralised patella tendon.

With the arrangement shown in FIG. 17, where the femoral component 210 (which is largely as per the femoral component described above in relation to FIGS. 12A through 12C with the addition of the cam 130) is fitted on the bearing component 111, and the knee is unflexed, the helical condylar parts 113 and 114 of the femoral component 210 will have point contact engagement with the corresponding bearing surfaces 115, 116. As the knee is flexed, there is relative sliding movement between the femoral component 210 and the bearing component 111, as the respective exterior surfaces of the condylar parts 113, 114 slide over the corresponding bearing surfaces 115, 116 of the bearing component, with the knee flexing up to 90°. During this initial flexion, for example up to approximately 70°, the cam 130 remains clear of the inner surface of recess 135. This angle could be varied as required, and indeed in another embodiment there could be no engagement between the surface of recess 135 and the cam 130 until an angle of flexion of approximately 90° is reached. When the particular angle is reached, however, the cam 130 enters the recess 135 defined by the peg 132 and the matching of the external surface of the cam 130 with the internal surface of the recess 135 enables the relative sliding movement between the femoral component 210 and the bearing component 111 to continue with the femoral component 210 effectively being pulled back due to engagement of the cam 130 in the recess 135. Thus, contact is maintained beyond 90°, for example up to approximately 160° or whatever maximum flexion is with any given patient, due to the cam 130 engaging against and following the form of the interior surface of the recess 135, thereby allowing continued flexion of the knee. Furthermore, the fact that the condyles are unconstrained in the antero-posterior direction allows the femoral component 210 to move backwards as the cam 130 is engaged in the recess 135, without affecting the lateral translation of the femoral component due to the helical nature of the condyles and the correspondingly angled nature of the bearing surfaces 115, 116.

Medial and Posterior Stabilised Design

FIGS. 18 and 19 show two different types of knee, each of which has drawbacks.

Figure 18C:
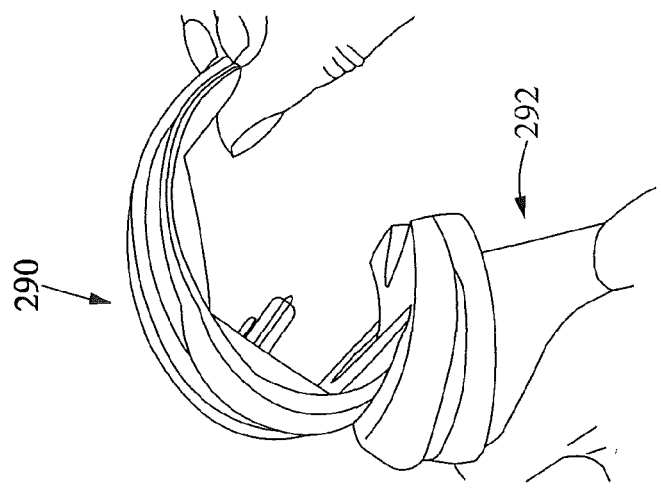
FIGS. 18a to 18c show a medial rotation knee which is not according to the present invention at varying flexion angles.
Figure 18B:
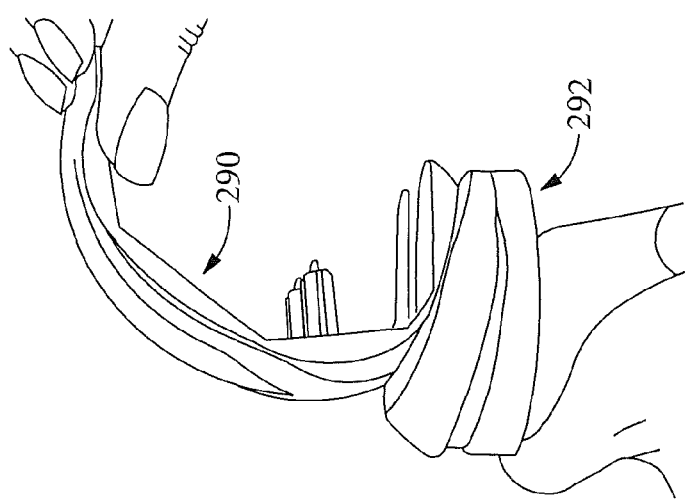
Figure 18A:
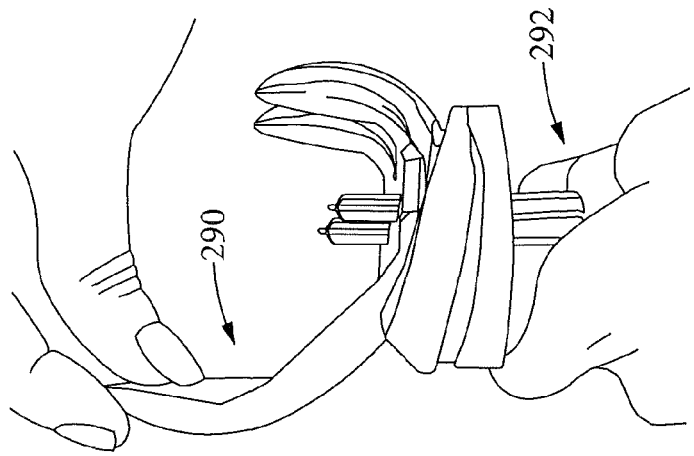

FIGS. 18a to 18c show a medial rotation knee in which the knee pivots for twisting on the medial condyle and respective bearing surface. This is shown in various stages of flexion. The femoral component 290 has two condyles which have a single radius.

These each sit on a respective tibial bearing surface on a tibial component 292. This knee has a disadvantage though at high flexion, where the posterior edge of the tibial component interferes with and abuts the femur at high flexion and effectively prevents high flexion angles from being possible. The problem is that the single radius design femoral component moves forward on the tibial component as shown in FIG. 18c, causing impingement between the posterior femur and the posterior edge of the tibial component.

Figures 19A, 19B, 19C:
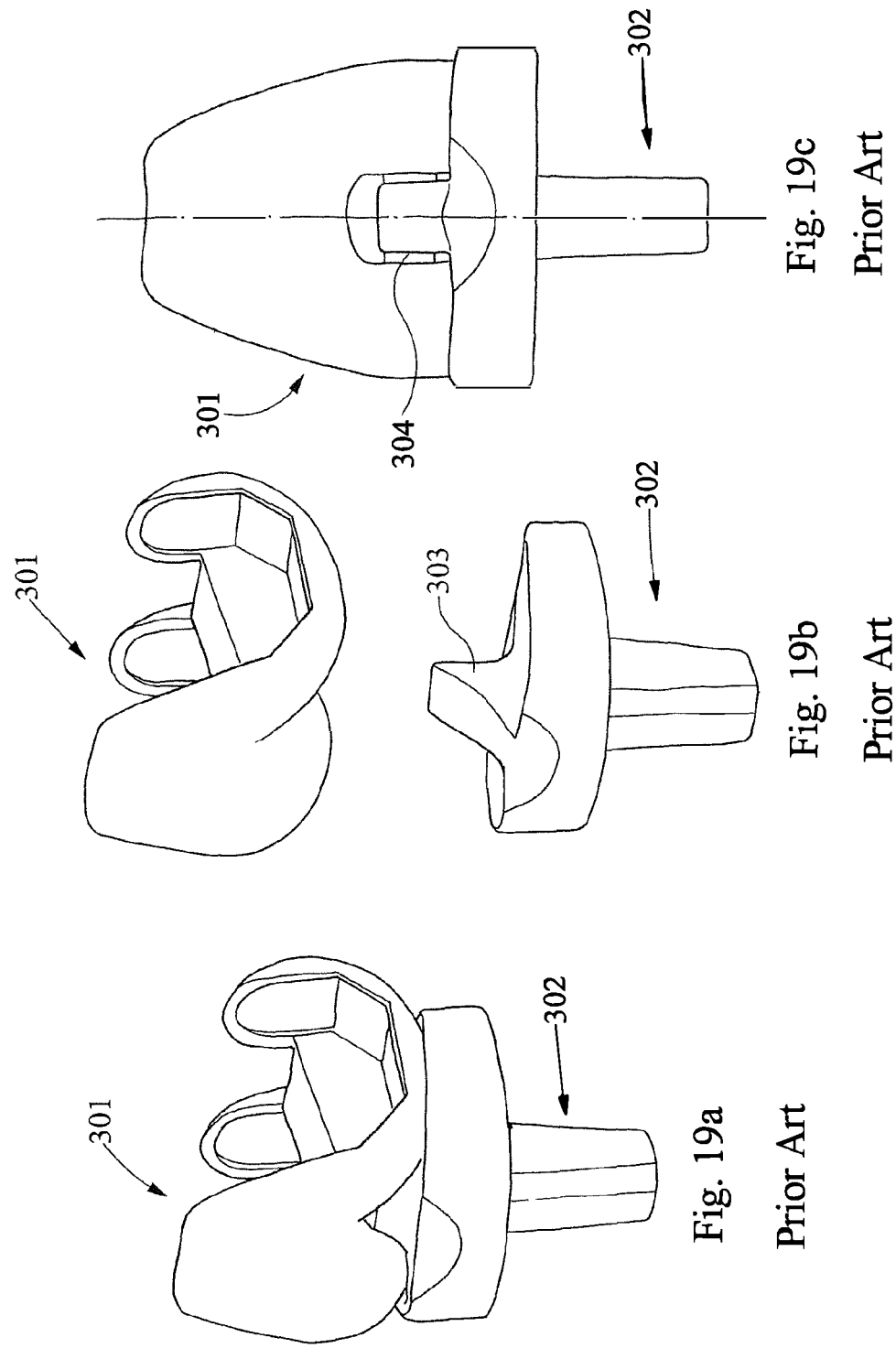
FIGS. 19a to 19i show a posterior stabilised knee prosthesis which is not according to the present invention.
Figure 19G:
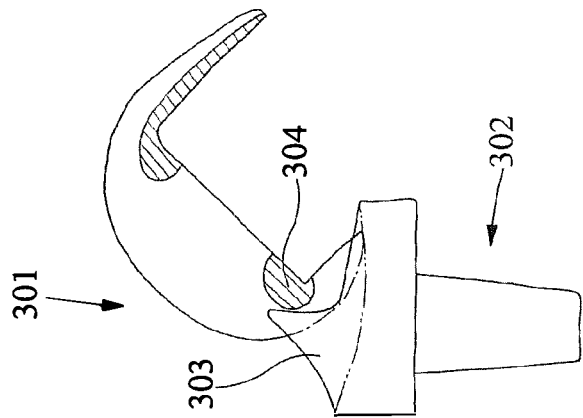
Figure 19F:
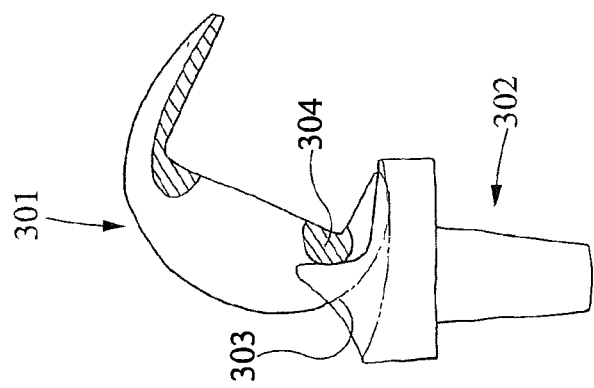
Figure 19E:
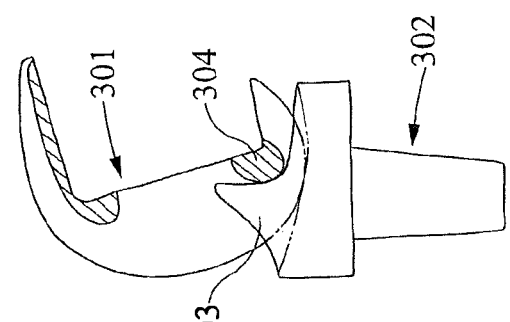
Figure 19D:
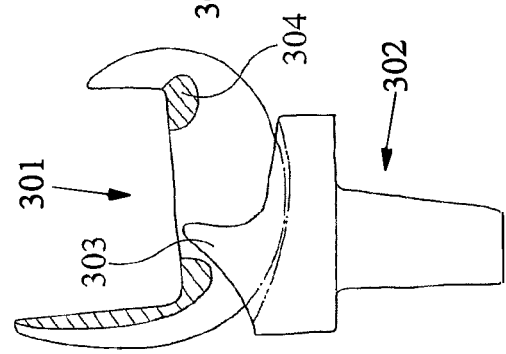
Figure 19H:
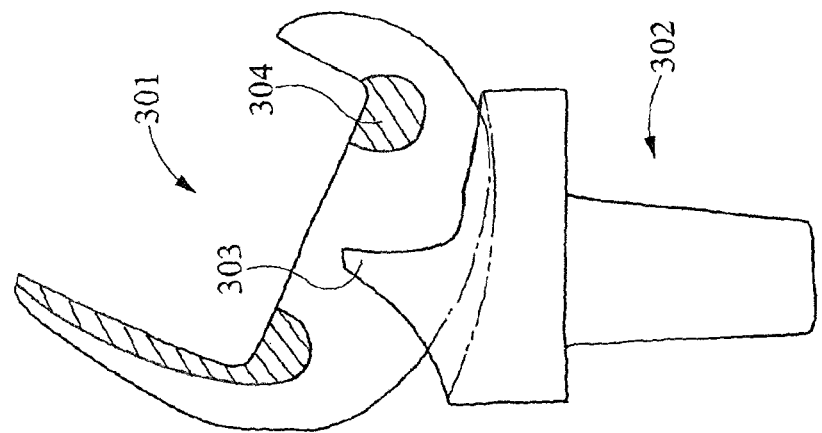
Figure 19I:
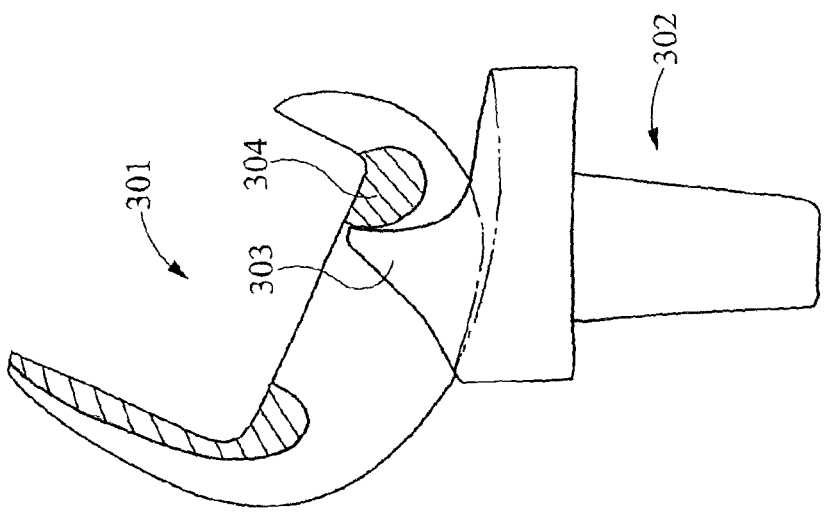

FIGS. 19a to 19i show a different kind of knee joint: a posterior stabilised knee. This knee overcomes the disadvantage provided by the medial rotation knee by providing a cam 304 on the femoral component 302 and a peg 303 on the tibial component 301. At high flexion, the cam 304 and peg 303 engage to pull the femoral component back on the tibial component, to ensure that, even at high flexion angles, the femur does not abut against the posterior of the tibial component. This is shown most clearly in FIGS. 19d to 19g, which show no flexion, 80 degree flexion, 120 degree flexion and 140 degree flexion respectively. This engagement of the femoral and tibial components provides stability in high flexion. However, as shown in FIGS. 19h and 19i, which show the joint at around 30 degrees flexion, this causes gross antero-posterior instability at low flexion angles, where the femoral component can move anteriorly and posteriorly relative to the tibial component, leading to a loss of stability in the joint. Without the engagement of the cam and peg at low angles, there is no stabilisation of the joint, and the femoral component is free to skid across the tibial component antero-posteriorly. FIG. 19h shows the femoral component 301 displaced anteriorly relative to the tibial component 302, while FIG. 19i shows the femoral component 301 displaced posteriorly relative to the tibial component 302.

Figure 20:
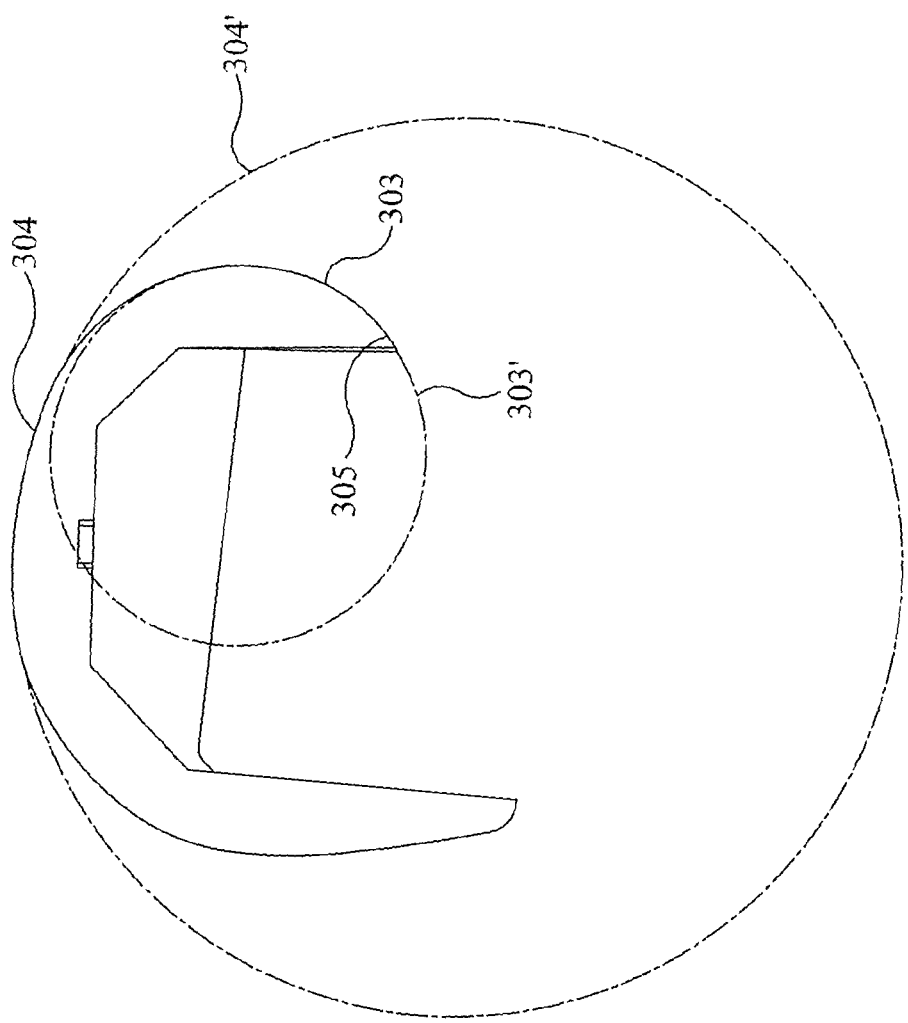
FIG. 20 shows the femoral component of FIG. 19, with extension and flexion arcs extrapolated to full circumferences.

FIG. 20 shows the "J" profile of such a condyle of a femoral component described above. The "J" is made up of a large radius 304, forming part of a large notional circumference 304', in a region which contacts a tibial bearing surface during extension of the knee, and a smaller radius 303, forming part of a small notional circumference 303', in a region which contacts a tibial bearing component during flexion of the knee. This emulates a femur. However, at high flexion, the posterior end 305 of the condyle, which is sharp, will tend to dig into the tibial bearing surface and prevent smooth flexion of the joint.

Figure 21A:
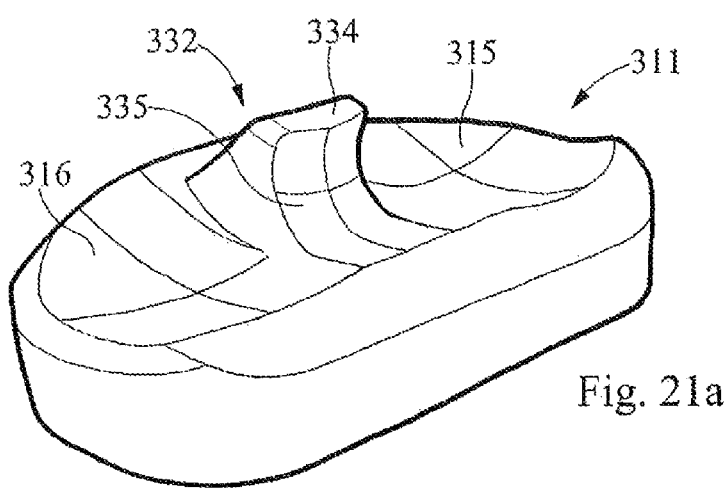
FIGS. 21a and 21b show a tibial component of a knee prosthesis according to a further embodiment of the invention.
Figure 21B:
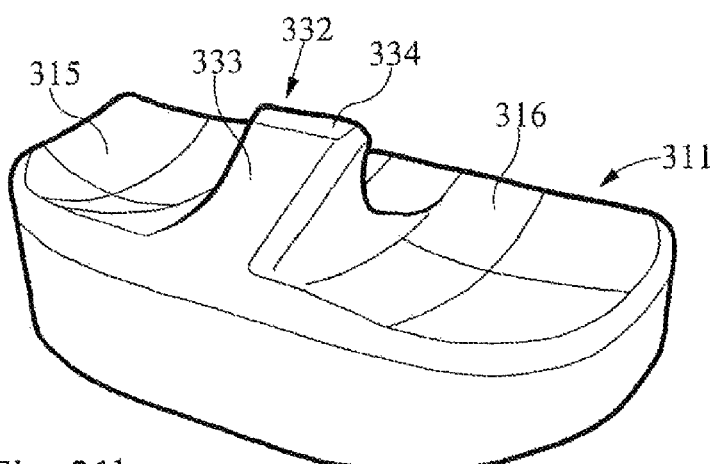

Embodiments described herein can be used to limit this gross instability at low flexion angles by providing congruent surfaces of one of the condyles and its respective bearing surface at low angles of flexion, together with a cam and peg to provide posterior stabilisation at high flexion angles. In this regard, FIGS. 21a and 21b show a tibial component 311 of a knee prosthesis of a further embodiment of the invention. The knee prosthesis is similar to those described above in relation to earlier embodiments of the invention described above, and similarly named parts, components and functions will not be described in detail again, their description being as described above unless context or the description of this embodiment clearly shows to the contrary.

The tibial component 311 is similar to, but different from, those described above in relation to FIGS. 1 to 15. The cam and peg described in relation to FIGS. 16 and 17 are present in the present embodiment. In addition, as shown in FIGS. 23-25, a medial condyle 313 and respective bearing surface 315 are provided (together with a lateral condyle 314 and corresponding tibial bearing surface 316). The medial condyle 313 and respective tibial bearing surface 315 are congruent in this embodiment, at least in the contact portions at low flexion. Congruent engagement of condyle and respective tibial bearing surface has been described in earlier embodiments above. In the present embodiment, the medial condyle 313 is part-helical and congruent with the bearing surface 315, and the lateral condyle 314 is also part-helical. The lateral tibial bearing surface is not part helical. The present embodiment of the invention is not limited to such part-helical condyles, but can be applied to non-helical condyles and congruent bearing surfaces.

FIG. 21 also shows a peg 332 on the tibial component 311, which is as described above with reference to FIGS. 16 and 17. The peg 332 engages with a cam 330 (shown in FIGS. 23 to 25) on the femoral component 311, which together form interengaging means, to form a posterior stabilised knee joint in a similar manner as described with regard to FIGS. 16 and 17 above. In particular, as described above, in the present embodiment, the cam and peg engage at angles of flexion higher than a predetermined angle, in the present embodiment around 80 degrees. At angles higher than this, the femoral and tibial components are retained in contact with the cam 330 and peg 332 minimising antero-posterior movement.

FIGS. 22*a-h* show various plan, elevation and cross-sectional views of the tibial component 311 of FIGS. 21*a* and 21*b*. FIG. 22*a* shows a plan view onto the tibial component 311. The medial and lateral bearing surfaces 315, 316 are shown in FIG. 22*a* and the cross section of FIG. 22*b*. As shown most clearly in FIG. 22*b*, the medio-lateral arc of the medial bearing surface 315 has a smaller radius than the curve of the lateral bearing surface 316.

FIG. 22*c* shows a side elevation of the tibial component 311. The peg 332 is shown. FIG. 22*d* shows a horizontal cross section through the peg 332 of FIG. 22*c*. This clearly shows that the recessed surface 335 of the peg 332 is curved in a plane substantially parallel to a plane through both bearing surfaces 315, 316. This allows the cam to rotate about the curve of the peg 332 in that plane, to allow rotation of the joint at high flexion when the cam 330 and peg 332 are engaged. This allows the femoral and tibial components to twist by a small amount relative to one another when the joint is at higher flexion angles at which the joint is posterior stabilised by the engagement of the cam 330 and peg 332 of the interengaging means.

FIG. 22*e* shows a main elevation of the tibial component 311 from a posterior direction. FIG. 22*f* shows a cross section through the tibial component in the region of the medial bearing surface 315 in the antero-posterior direction. It can be seen that the medial bearing surface has a substantially arcuate surface in the antero-posterior direction. Turning now to FIG. 22*h*, which is a cross-section through the tibial component in the region of the lateral bearing surface 316 in the antero-posterior direction, it can be seen that the curvature of the lateral bearing surface 316 is much more open than that of the medial bearing surface 315, to allow for antero-posterior translation on the lateral side along the bearing surface 316. Returning to FIG. 22*g*, this shows a cross section through the tibial component 311 in the region of the peg 332, and shows the recessed curvature of the surface 335 as the peg 332 extends away from the tibial component 311.

In the present embodiment, the medial condyle 313 and bearing surface 315 are part spherical—i.e. they comprise a single radius in both the medio-lateral, and antero-posterior directions in the contact portions at low flexion of the prosthesis. In this way, the medial condyle 313 and corresponding bearing surface 315 together form a shallow ball and socket joint. The lateral tibial bearing surface 316 is incongruent with the lateral condyle 314 at all angles of flexion to allow for antero-posterior movement on the lateral side, caused by twisting rotation about the medial condyle 313, as described in more detail below. In particular, while the lateral bearing surface 316 comprises a curve in the present embodiment in the antero-posterior direction, this curve is of significantly greater radius than the lateral condyle of the femoral component. This provides for rotation of the knee about an axis extending through one (in this embodiment the medial) condyle. In the present embodiment, the lateral bearing surface 316 is also curved in the medio-lateral direction. In alternative embodiments of the invention this medio-lateral curvature is the same as the medio-lateral curvature of the lateral condyle and follows an arc, centred around the centre of rotation of the medial condyle and bearing surface, to provide a guide for the rotation of the lateral condyle 314 on the lateral bearing surface 316.

FIGS. 23*a* and 23*b* show a full knee prosthesis comprising a tibial component 311 as described with reference to FIGS. 21 and 22, with a corresponding femoral component 310. As shown in both figures, the medial and lateral condyles 313, 314 sit on respective medial and femoral bearing surfaces 315, 316. An intercondylar groove is provided between the two condyles 313, 314. At the posterior side, as in previous embodiments, the cam 330 is positioned at the back of an intercondylar box, and extends across between the two condyles 313, 314. In FIGS. 23*a* and 23*b* the knee is flexed at an angle of around 30 degrees. The medial condyle 313 sits in the congruent tibial bearing surface 315 in both FIGS. 23*a* and 23*b*. However, in FIG. 23*a*, the lateral condyle 314, and thus the whole femoral component 310, is rotated (twisted) about the medial condyle 313, pushing the lateral condyle 314 toward the posterior of the joint, while still sitting on the lateral bearing surface 316. FIG. 23*b* shows the same joint, but with the lateral condyle 314 pushed towards the anterior of the joint, while again still sitting on the lateral bearing surface 316. In this way, overall antero-posterior relative movement of the tibial and femoral components 311, 310 is avoided, while twisting rotation of the joint is enabled by the provision of the congruent medial side 313, 315 providing a pivot point for the joint, with the antero-posterior movement of the lateral side 314, 316. In FIG. 23, as the angle of flexion is only around 30 degrees, the cam 330 and peg 332 are not engaged to provide antero-posterior stability, so, at this angle this stability is provided only by the congruent surfaces of the condyle 313 and bearing surface 315 on the medial side.

FIGS. 24*a* and 24*b* show the knee prosthesis of FIGS. 23*a* and 23*b* but at an angle of flexion of around 120 degrees. At this flexion angle, the cam 330 of the femoral component 310 is engaged with the curved surface 335 of the peg 332 to engage and bring the femoral component 310 into a posterior position in relation to the tibial component 311. At this angle of flexion, the engaging surface of the medial condyle 313 is not congruent with the corresponding bearing surface 315. As the prosthesis flexes from the angle of around 30 degrees shown in FIG. 23 to the angle of around 120 degrees shown in FIG. 24, the surface profile of the medial condyle 313 changes from one which is congruent with the corresponding bearing surface 315 to allow the movement described above, to one which is incongruent. This occurs as the flexion radius of the medial condyle 313 is smaller than the fixed radius of the corresponding bearing surface 315. This change may occur gradually at an angle between 60 and 120 degrees, 70-110, 80-100, or 85-95 degrees for example. Thus, at relatively high flexion, both condyles 313, 314 are incongruent with their respective bearing surfaces 315, 316. Therefore, the these regions of the condyles 313, 314 do not prevent the antero-posterior movement of the femoral component 310 relative to the tibial component 311, while at low flexion, in extension, the condylar surface 313 is congruent with the tibial bearing surface 315. As the radius decreases, the surfaces become incongruent. However, the peg 332 of the interengagement means also engages with the cam 330 at these higher flexions, as shown in the cross section of the view of FIG. 25a in FIG. 25b, and this thus limits the antero-posterior movement of the femoral component 310 relative to the tibial component 311. As the flexion increases further, the engaging surface of the femoral component moves towards the posterior rounded edge of the condyles (317, 318 in FIG. 23b) which are rounded to a further reduced radius on the tibial bearing surface 315, and thus allowing greater ease of twisting of the joint, while minimising contact between the posterior edges of the femoral component and the tibial bearing surfaces to minimise those femoral component posterior edges digging into the tibial bearing surfaces.

As neither the lateral nor medial sides are congruent between condyles 313, 314 and bearing surfaces 315, 316, at these high flexion angles, antero-posterior movement of each individual condyle is possible—twisting in one sense individually moving the medial condyle anteriorly and the lateral condyle posteriorly about the cam 330 and peg 332, and twisting in the other sense reversing the movement. The movement of the two condyles 313, 314 is substantially equal and opposite, thus preventing substantial antero-posterior movement of the femoral component 310 as a whole relative to the tibial component 311.

With the prosthesis of this embodiment, comprising congruent medial condyle and bearing surface, together with non-congruent lateral condyle and bearing surface at low flexion, and a cam on the tibial component and peg on the femeral component, antero-posterior movement can be minimised both at low flexion and at high flexion.

In the present embodiment, the twisting rotation of the joint at low angles of flexion is about the medial condyle 313 and bearing surface 315, and it is the medial condyle 313 and respective bearing surface 315 that are congruent. However, this could be changed to the lateral condyle 314 and bearing surface 316. The other, non-congruent condyle and bearing surface, in the present embodiment the lateral condyle 314 and bearing surface 316 then allow twisting of the knee joint by antero-posterior movement of the non-congruent condyle 314, pivoting about the congruent condyle 313.

In alternative embodiments, not shown, the medial (or lateral, if a lateral pivoting joint, rather than a medial pivoting joint) condyle and bearing surface may not be completely congruent. If the longitudinal radius and transverse radius of the femoral condyle are different, it is not possible to have congruent contact while allowing rotation. However, as long as there is front to back conformity of the tibial bearing surface with the femoral condyle, instability is prevented and, because it is not congruent, rotation is allowed. The femoral and tibial components may be formed from the same materials as described in relation to other embodiments.

Some embodiments of the present invention can enable congruent contact to be maintained between at least one femoral condyle and the bearing component throughout a range of flexion of the knee, e.g. for at least 0-60°. Where provided, the helical nature of the condyles has the effect of laterally displacing the patella groove. Moreover the form of the condyles upon movement, i.e. flexing, of the knee induce a lateral translatory movement of the femur upon the tibia with increasing flexion of the knee, thus further displacing laterally the patella groove. In addition, the fact that at least one of the condyles is unconstrained in at least an antero-posterior direction allows the femoral component to shift backwards with respect to the tibial component, without the need for a separate mobile bearing component.

As a consequence of the above, it will be appreciated that this knee replacement design more faithfully reproduces the natural position of the patella groove on the prosthetic femoral component, so that desired lateral patella tracking is more faithfully achieved, thereby reducing pain and morbidity. It will also be appreciated that this required tracking is achieved without any removal of the lateral femoral condyle and without the need for a mobile bearing component.

The following description explains in more detail the behaviour of the femoral component relative to the tibial bearing component. This is described independently of the behaviour of the tibial bearing component relative to a tibial baseplate (not shown) which, for the purposes of this description is fixed with respect to the tibia.

The behaviours are controlled in part by the relative geometries of the condyles, but also by the engaging mechanism employed, which may be a cam/post arrangement or a ball and socket arrangement. The engaging mechanism when engaged prevents translation of the femoral component relative to the tibial bearing component, but will allow rotational motion by virtue of having rounded engaging surfaces. Such a rounded surface can be applied to a post for engagement on a cam of prismatic section. With equal effect a rounded surface can be applied in convex form to the cam, which, when the radius is sufficiently large, can be described as a sphere. In some embodiments, the rounded surface of the post can be applied in concave form to form a socket. Thus, the engaging mechanism can be described as a ball and socket.

Both a cam/post arrangement and a ball/socket arrangement, when they are engaged, are characterised by having a rotation centre, in flexion and extension, which is collinear with a centre of a radius of a posterior portion of the femoral condyles. Moreover, an axis of rotation of the cam/post or ball/socket arrangement is co-axial with an axis of rotation of the posterior portion of the femoral condyles. This ensures that, when the cam/post or ball/socket arrangement is engaged, the femoral component rotates around the rotation centre whilst still permitting rotation in a medial or lateral direction.

Figures 26A, 26B:
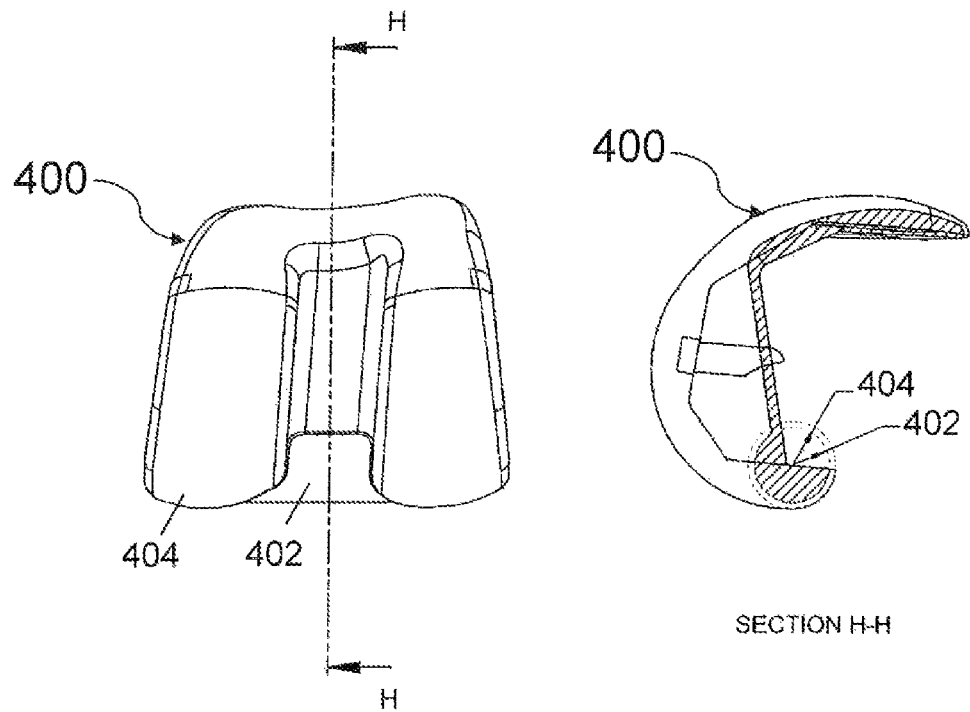
FIGS. 26a and 26b show respectively, a front view and a side cross-sectional view through a cylindrical prism cam, of a femoral component in accordance with an embodiment of the invention.

FIGS. 26a and 26b show respectively, a front view and a side cross-sectional view through a cylindrical prism cam 402, of a femoral component 400 in accordance with an embodiment of the invention. As shown best in FIG. 26b, the centre of rotation of the cam 402 is coincident with a centre of rotation of a posterior portion of the condyles 404.

Figures 27A, 27B:
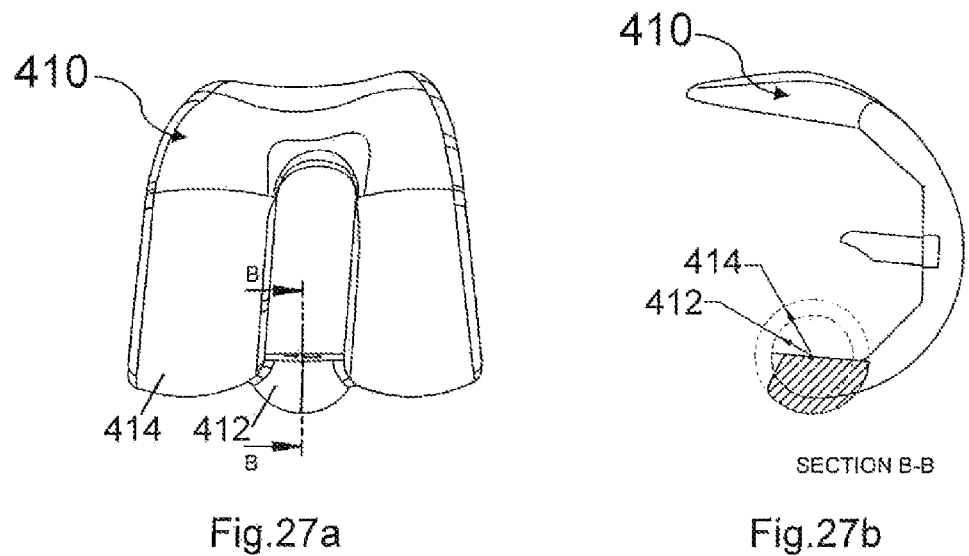
FIGS. 27a and 27b show respectively, a front view and a side cross-sectional view through a part-spherical ball-shaped cam, of a femoral component in accordance with an embodiment of the invention.

FIGS. 27a and 27b show respectively, a front view and a side cross-sectional view through a part-spherical ball-shaped cam 412, of a femoral component 410 in accordance with an embodiment of the invention. As shown best in FIG. 27b, the centre of rotation of the cam 412 is coincident with a centre of rotation of a posterior portion of the condyles 414.

Figures 28A, 28B:
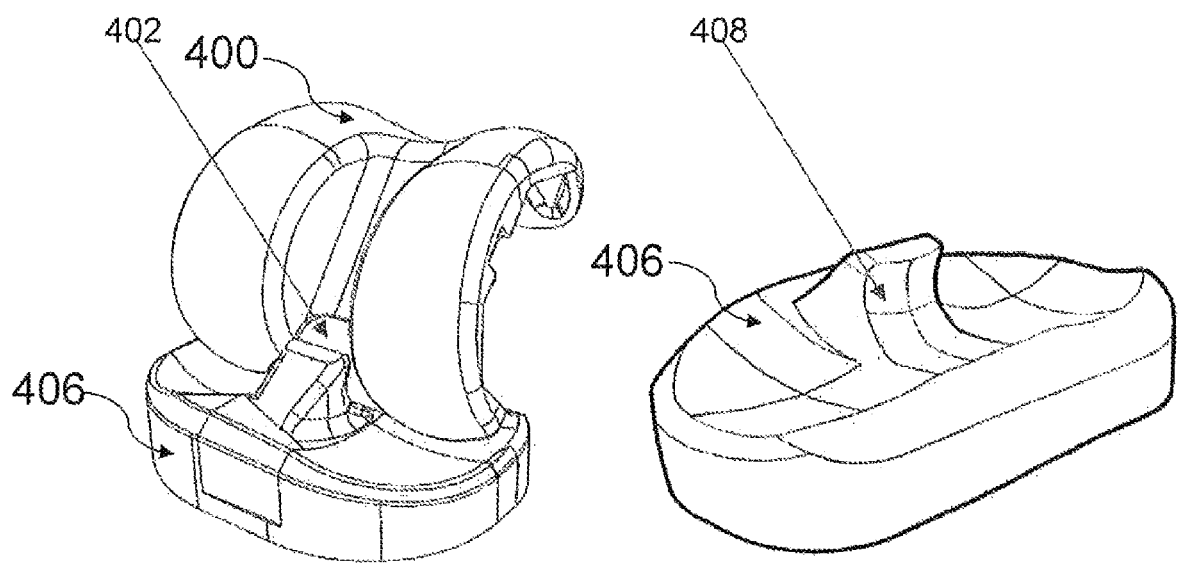
FIGS. 28a and 28b show respectively, a front perspective view of the femoral component of FIGS. 26a and 26b in engagement with a tibial component including a complementary post, and a rear perspective view of said tibial component alone.

FIGS. 28a and 28b show respectively, a front perspective view of the femoral component 400 of FIGS. 26a and 26b in engagement with a tibial component 406 including a complementary post 408, and a rear perspective view of said tibial component 406 alone.

Figures 29A, 29B:
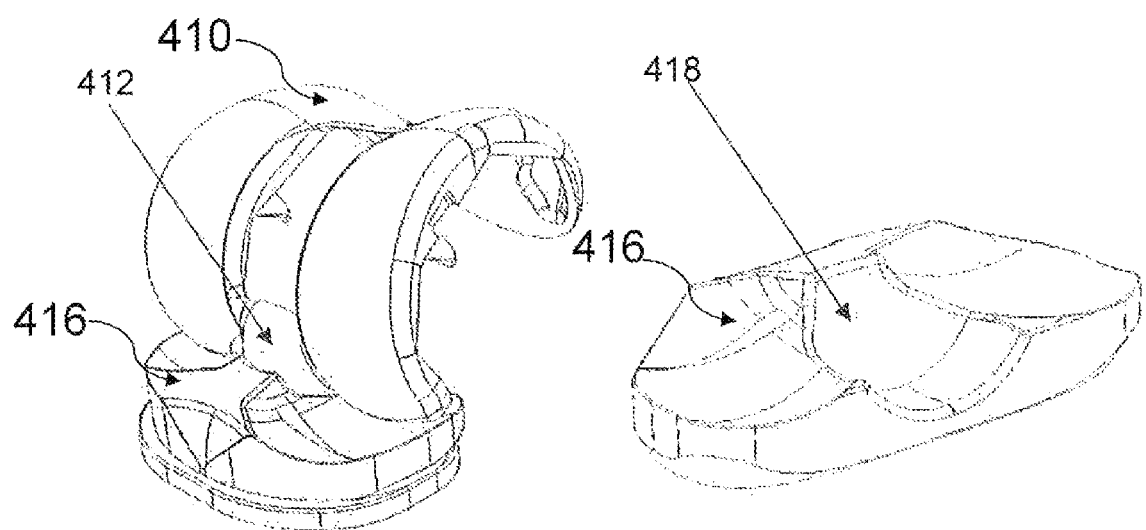
FIGS. 29a and 29b show respectively, a front perspective view of the femoral component of FIGS. 27a and 27b in engagement with a tibial component including a complementary socket, and a rear perspective view of said tibial component alone.

FIGS. 29a and 29b show respectively, a front perspective view of the femoral component 410 of FIGS. 27a and 27b in engagement with a tibial component 416 including a complementary socket 418, and a rear perspective view of said tibial component 416 alone.

The following description describes in detail the behaviour of prosthesis according to embodiments of the invention, at different angles of flexion. Although the drawings are based on the femoral component 400 and tibal component 406, it will be understood that the same behaviour is exhibited by the femoral component 410 and the tibial component 416. Accordingly, the phrase cam/post and ball/socket are interchangeable.

The behaviours of the femoral component 400 relative to the tibial component 406 are described in a number of zones bounded by 0 to 75 degrees of flexion, 75 to 90 degrees, 90 to 110, and finally 110 degrees and above. These angle ranges were verified on actual models to avoid speculation.

Figures 30A, 30B:
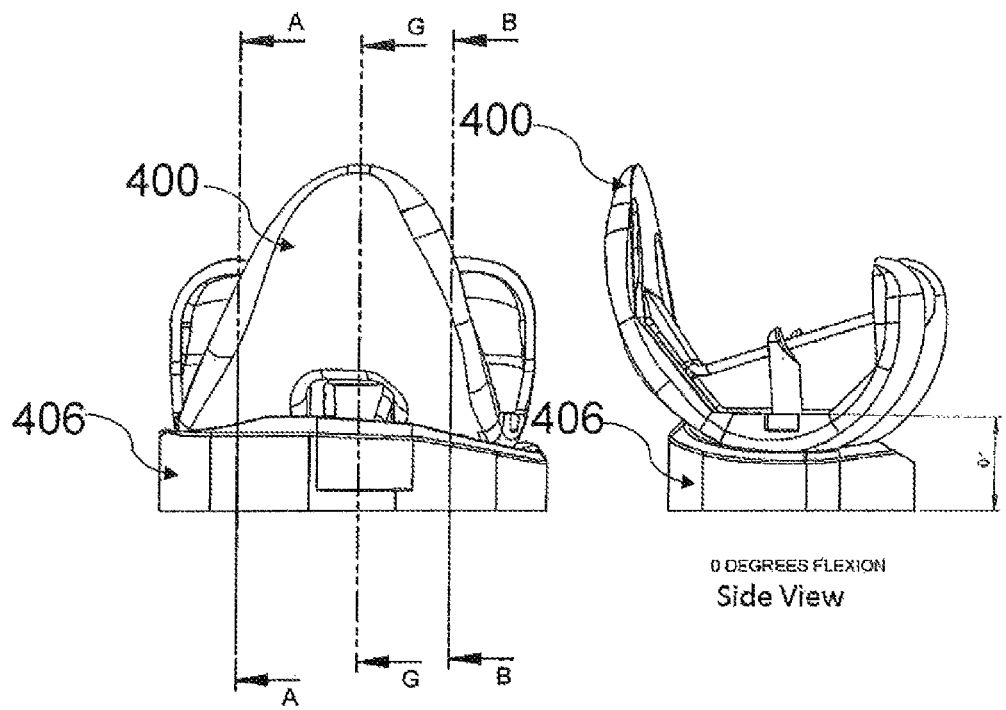
FIGS. 30a, b and c show respectively a front, side and top view of a prosthesis similar to that of FIG. 28a at 0 degrees of flexion and FIGS. 30d, e, f and g show respectively cross-sectional views along lines AA, BB, CC and GG shown in FIGS. 30a and c.
Figure 30C:
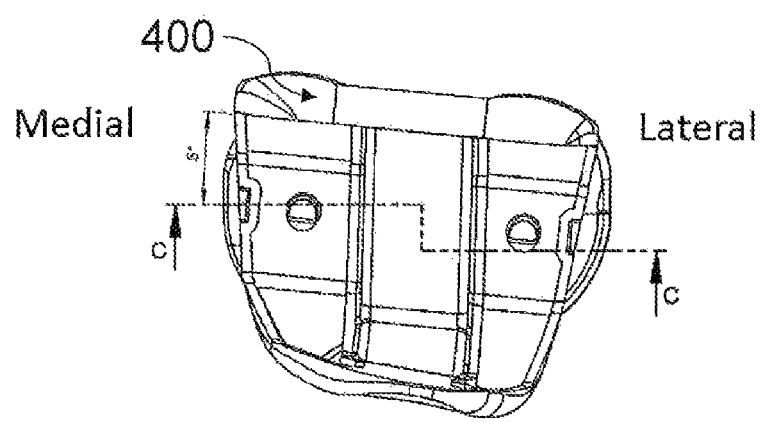
Figures 30D, 30E:
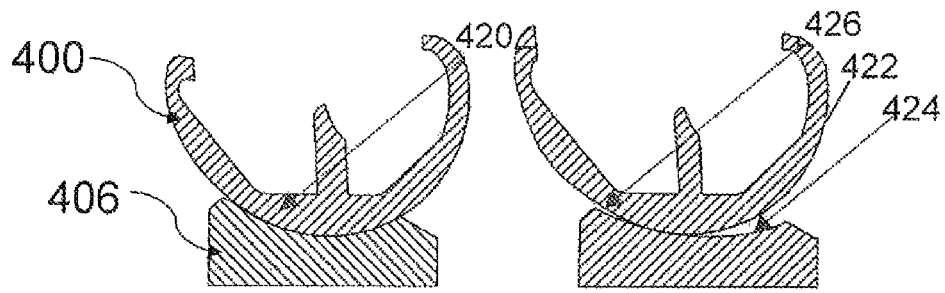
Figure 30F:
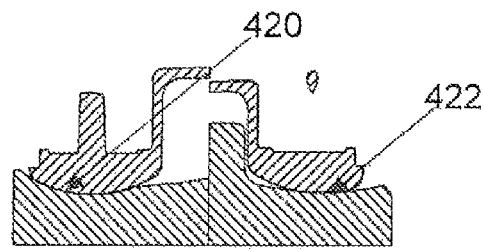
Figure 30G:
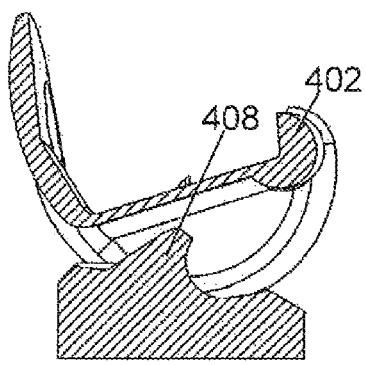
Figures 31A, 31B:
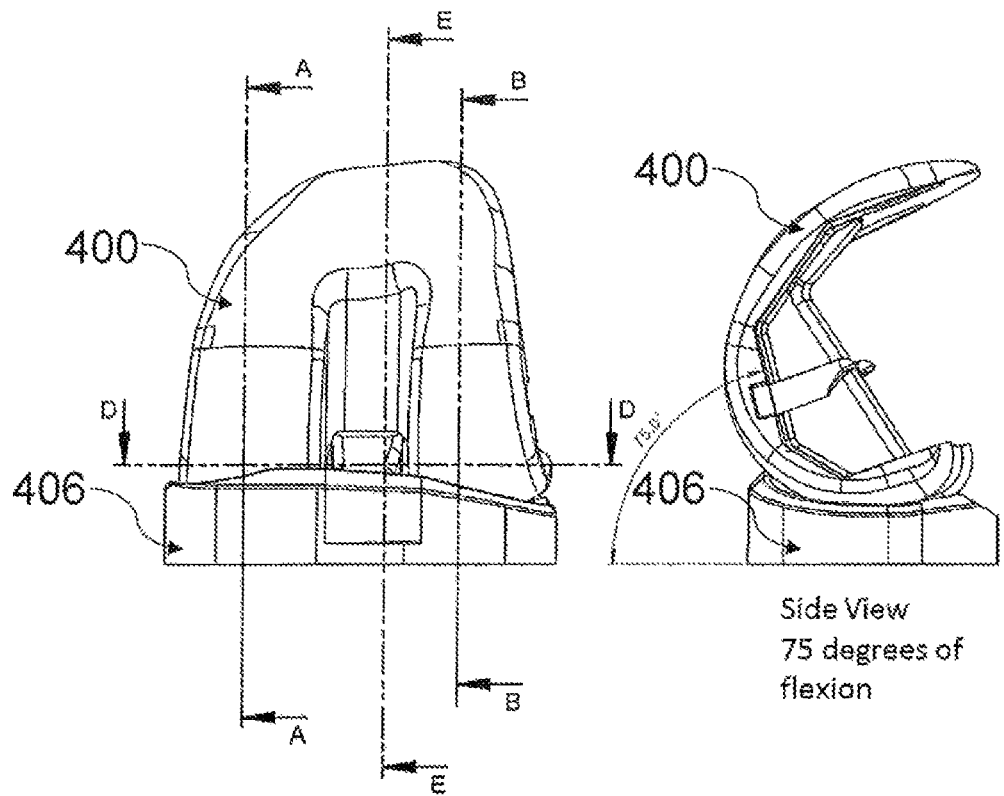
FIGS. 31a, b and c show respectively a front, side and top view of a prosthesis similar to that of FIG. 28a at 75 degrees of flexion and FIGS. 31d, e, f and g show respectively cross-sectional views along lines AA, BB, CC and EE shown in FIGS. 31a and c.
Figure 31C:
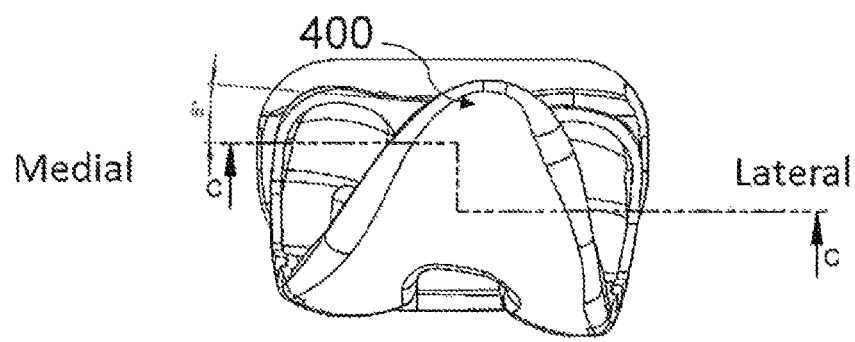
Figures 31D, 31E:
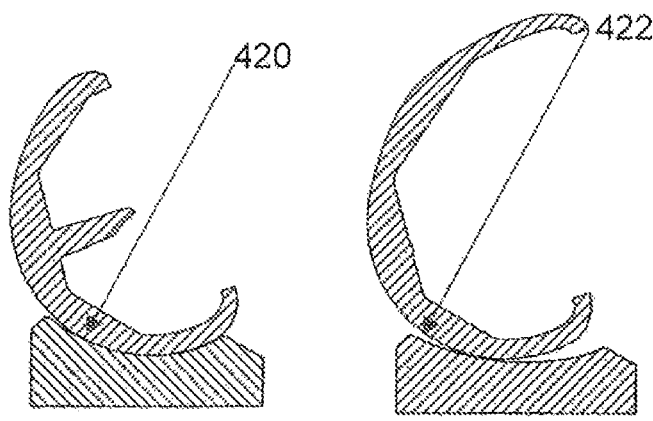
Figure 31F:
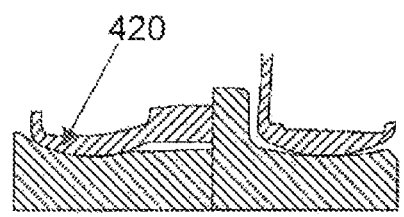
Figure 31G:
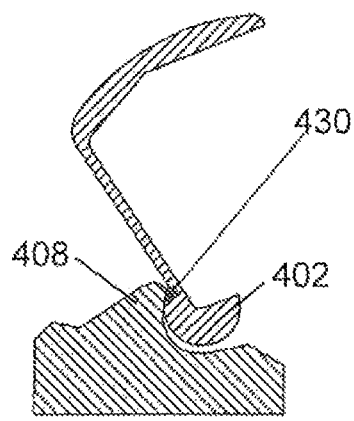

Between 0 and 75 degrees (as shown in FIGS. 30a to g at 0 degrees flexion), a medial condyle 420 is congruent with a respective bearing surface of the tibial component 406, whilst a lateral condyle 422 is incongruent with a respective bearing surface of the tibial component 406 (at least in a posterior region 424). The lateral condyle 422 is therefore uncontrolled at least until an anterior portion 426 of the lateral condyle 422 engages on a raised anterior periphery of the tibial component 406. At this point a limit of internal rotation is reached. In a normal knee from zero until 140 degrees of flexion, the lateral condyle gradually translates backwards on the tibia. With the present knee replacement design, uncontrolled movement of the lateral condyle 422 forwards and backwards through an arc of 10 degrees is possible (i.e. +−5 degrees, and 5 degrees of internal rotation is shown as illustrated in FIG. 30c). However, in reality, the lateral condyle 422 tends to skid forwards and stay forwards between 0 and 75 degrees of flexion as shown in FIG. 30e.

At start a transition angle, which in this case is 75 degrees as shown in FIGS. 31a to g, cam 402 and post 408 contact 430 occurs. At this point fully congruent contact of the medial condyle 420 and cam/post contact 430 encourage posterior translation of the lateral condyle 422 away from the anterior edge of the lateral bearing surface of the tibial component 406, thus starting to induce external rotation.

Figures 32A, 32B:
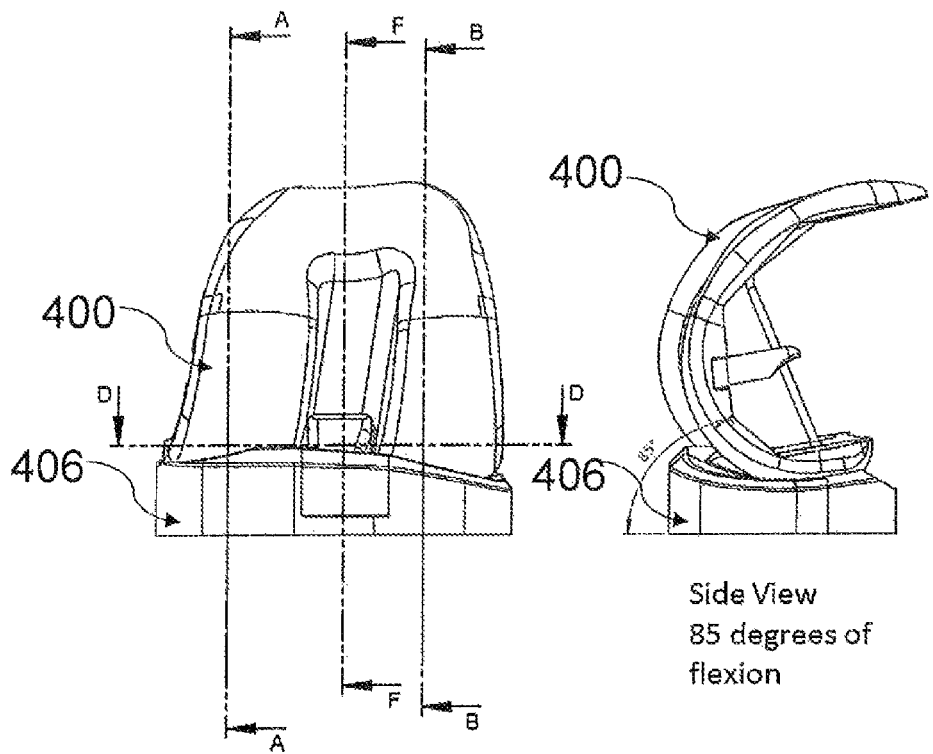
Figure 32C:
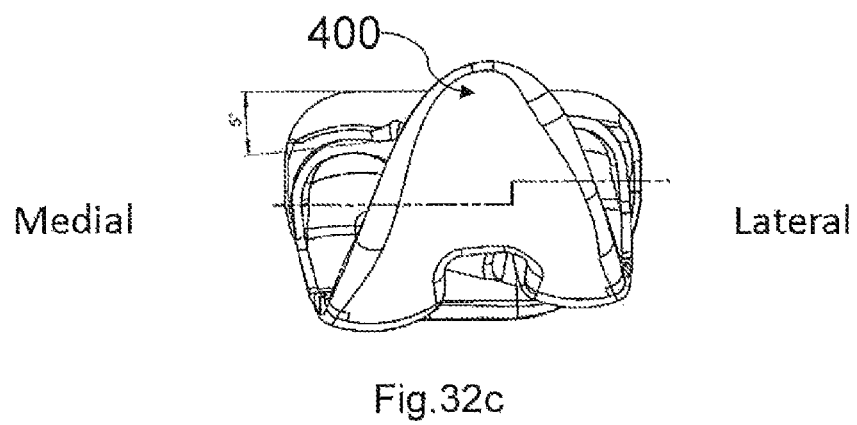
Figures 32D, 32E:
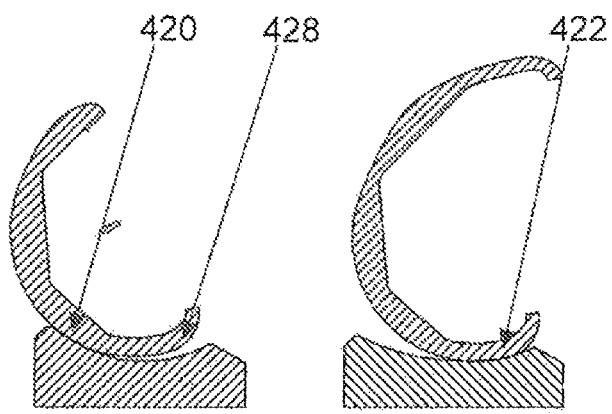
Figure 32F:
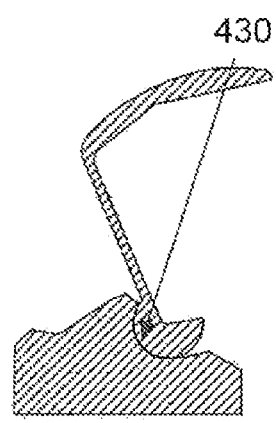
Figures 33A, 33B:
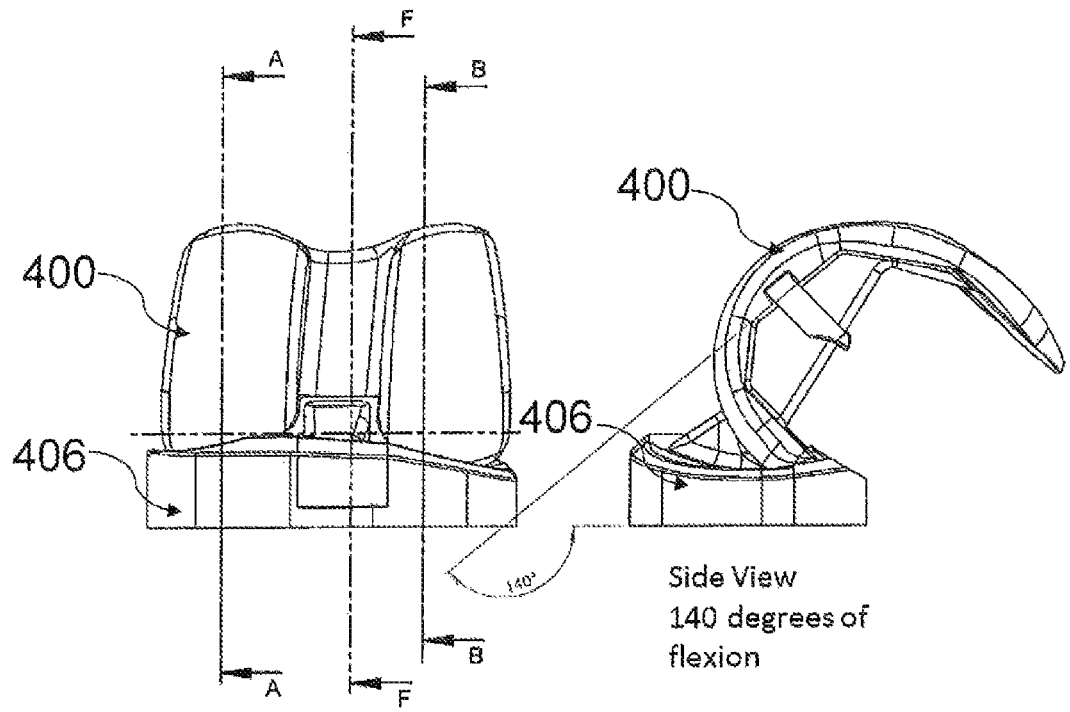
Figure 33C:
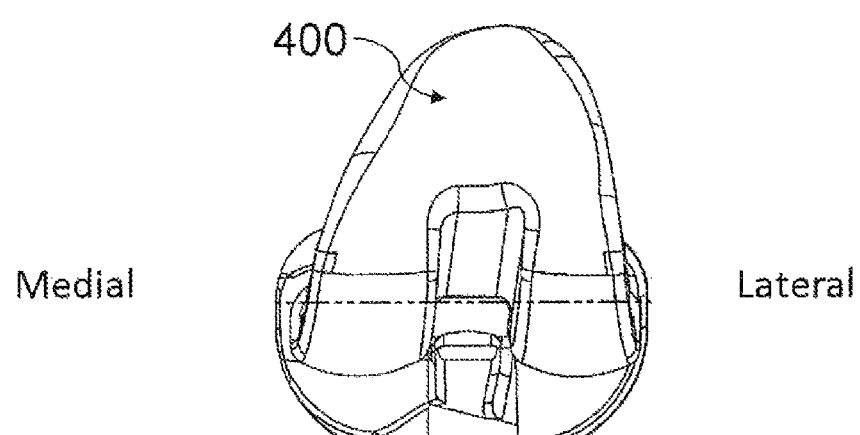
Figures 33D, 33E:
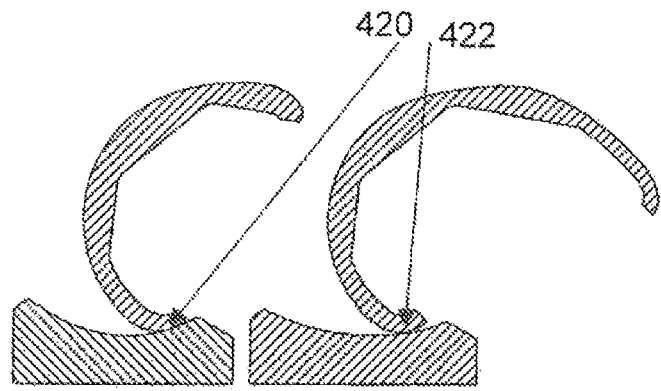
Figure 33F:
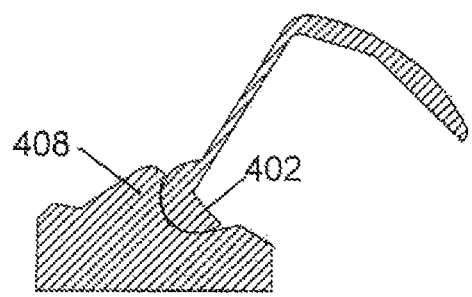

As 90 degrees of flexion is approached (shown in FIGS. 32a to f at 85 degrees), the posterior side 428 of the medial condyle 420 becomes incongruent whilst the anterior side of the medial condyle 420 and respective bearing surface remain in contact. This encourages external rotation about the cam/post causing translation posteriorly of the lateral condyle 422 and hence external rotation (the lateral condyle 422 is shown in FIG. 32e translated backwards giving 5 degrees of external rotation), and thus providing a powerful mechanism of inducing near natural kinematics of the system. However, at and above 90 and below 110 degrees, whilst the medial condyle 420 cannot translate forwards it can, if allowed by soft tissues, translate backwards. At greater than 110 degrees of flexion (shown in FIGS. 33a to f at 140 degrees), both the medial condyle 420 and the lateral condyle 422 are no longer congruent nor able to be restrained by the anterior raised edges of the tibial component 406. In this case, the contact moves to the posterior rounded edges of both condyles 420, 422, whereby both internal and external rotation is possible, whilst simultaneous translation of both condyles 420, 422 is prevented by the cam/post 402, 408 engagement.

Also, although not shown in any of FIGS. 26a to 33f, at least one of the condyles may be part-helical in shape and the respective bearing surface of the tibial component may be correspondingly part-helical in at least a medio-lateral direction.

It will be appreciated by persons skilled in the art that various modifications may be made to the above embodiments without departing from the scope of the present invention. For example, features described in relation to one embodiment may be mixed and matched with features described in relation to one or more other embodiments.

The invention claimed is:

1. A knee prosthesis comprising:
    a femoral component for securement to a femur, the femoral component defining medial and lateral J-shaped condyles and an intercondylar groove; and
    a fixed bearing tibial component for securement to a tibia, the tibial component having respective bearing surfaces which are fixed with respect to both a tibial engaging component and a stabilising peg for securing the tibial component to a tibia, the respective bearing surfaces being shaped to engage with said condyles both during extension and also over a range of flexion, wherein:
    the femoral and tibial components together comprise interengaging features, for stabilising against antero-posterior relative movement of the femoral and tibial components at flexion above a first predetermined angle of 110 degrees, wherein both the medial and lateral condyles are incongruent and unconstrained in an antero-posterior direction with the respective bearing surfaces at angles of flexion above the first predetermined angle of 110 degrees to allow for roll-back of the femoral component relative to the bearing surfaces, tibial engaging component, and stabilising peg;
    one of the condyles and the respective bearing surface of the tibial component are fully congruent at angles of flexion below a second predetermined angle of at least 70 degrees;
    the other bearing surface is incongruent with the other condyle and is unconstrained in at least the antero-posterior direction at angles of flexion below the second predetermined angle of at least 70 degrees, so as to allow for antero-posterior movement of the femoral component relative to the bearing surfaces of the tibial component; and
    wherein a transition zone is provided at angles of flexion between the second and first predetermined angles, in the transition zone the interengaging features begin to contact and the one condyle becomes unconstrained at a posterior side of the one condyle while an anterior side of the one condyle remains in contact with the respective bearing surface, which encourages external rotation and posterior translation of the other condyle until the first predetermined angle is reached, wherein both internal and external rotation is permitted.

2. The knee prosthesis according to claim 1 wherein the interengaging features comprise a peg and cooperating cam or a ball and socket.

3. The knee prosthesis according to claim 2 wherein the cam or ball is formed in the region of the intercondylar groove of the femoral component and the peg or socket is formed in or projecting from the tibial component.

4. The knee prosthesis according to claim 2 wherein the cam or ball extends across the intercondylar groove from a medial side to a lateral side of the prosthesis.

5. The knee prosthesis according to claim 2 wherein a surface of the peg or socket which engages with the respective cam or ball is rounded so as to allow the surface of the cam or ball to rotate about the peg or socket in a plane substantially parallel to a notional plane passing through both bearing surfaces of the tibial component.

6. The knee prosthesis according to claim 2 wherein the knee prosthesis is rotatable from a first position in which said one condyle and respective bearing surface are fully congruent to a second position in which said one condyle and respective bearing surface are unconstrained in at least the antero-posterior direction, the cam or ball and respective peg or socket engaging on rotation of the knee prosthesis after leaving the first position.

7. The knee prosthesis according to claim 1 wherein the interengaging features have a centre of rotation that is co-axial with a centre of rotation of a posterior radius of at least one condyle.

8. The knee prosthesis according to claim 1 wherein the second predetermined angle is in a range between approximately 70 and 100 degrees.

9. The knee prosthesis according to claim 1 wherein the medial condyle and corresponding bearing surface are fully congruent at angles of flexion below the second predetermined angle.

10. The knee prosthesis according to claim 1 wherein a surface of the medial condyle and corresponding bearing surface are rounded with equal radius in both flexion and extension facets of the prosthesis.

11. The knee prosthesis according to claim 1 wherein at least one of the condyles has point or line contact, as opposed to area contact, with a respective bearing surface.

12. The knee prosthesis according to claim 1 wherein at least the bearing surfaces of the tibial component comprise a cross-linked polymer.

13. The knee prosthesis according to claim 1 wherein the condyles are shaped in the manner of the threads on a screw, and the respective bearing surface is shaped in the manner of threads cut in a complementary nut.

14. The knee prosthesis according to claim 1 wherein at least one of the medial and lateral condyles are part-helical in shape.

15. The knee prosthesis according to claim 14, wherein the lateral condyle is part-helical in shape and the respective bearing surface for the lateral condyle is configured for incongruent contact which is unconstrained in at least the antero-posterior direction.

16. The knee prosthesis according to claim 14, wherein the lateral condyle is non-helical and the respective bearing surface is configured for incongruent contact which is unconstrained in both the antero-posterior direction and the medio-lateral direction.

17. The knee prosthesis according to claim 1, wherein the other condyle is non-helical.

18. The knee prosthesis according to claim 1, wherein the medial condyle is part-helical in shape and is configured for fully congruent contact with a respective bearing surface which is correspondingly part-helical.

19. The knee prosthesis according to claim 1, wherein a transverse cross-section of one condyle is flat, curved or semi-spherical.

20. The knee prosthesis according to claim 1, wherein a transverse cross-section is different for each condyle.

* * * * *